US010064546B2

(12) United States Patent
Yamakawa et al.

(10) Patent No.: US 10,064,546 B2
(45) Date of Patent: Sep. 4, 2018

(54) OPHTHALMIC ANALYSIS APPARATUS AND OPHTHALMIC ANALYSIS PROGRAM

(71) Applicant: NIDEK CO., LTD., Gamagori, Aichi (JP)

(72) Inventors: Ai Yamakawa, Gamagori (JP); Norimasa Satake, Aichi (JP); Tetsuya Kano, Toyota (JP); Hisanori Torii, Gamagori (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 322 days.

(21) Appl. No.: 14/061,178

(22) Filed: Oct. 23, 2013

(65) Prior Publication Data

US 2014/0112562 A1  Apr. 24, 2014

(30) Foreign Application Priority Data

Oct. 24, 2012 (JP) ................. 2012-235206
Oct. 24, 2012 (JP) ................. 2012-235207
Oct. 24, 2012 (JP) ................. 2012-235208

(51) Int. Cl.
*G06K 9/00* (2006.01)
*A61B 3/00* (2006.01)
(Continued)

(52) U.S. Cl.
CPC .......... *A61B 3/0025* (2013.01); *A61B 3/0041* (2013.01); *A61B 3/102* (2013.01); *G06F 19/321* (2013.01)

(58) Field of Classification Search
CPC ..... G06F 19/321; A61B 3/102; A61B 3/0041; A61B 3/0025
See application file for complete search history.

(56) References Cited

U.S. PATENT DOCUMENTS 6,299,305 B1  10/2001  Miwa
7,145,979 B2 *  12/2006  Urushiya ............... A61B 6/032
378/15
(Continued)

FOREIGN PATENT DOCUMENTS

JP   2000237135 A    9/2000
JP   2003-325500 A   11/2003
(Continued)

OTHER PUBLICATIONS

Boer et al. "Improved signal to noise ratio in spectral domain compared with time domain optical coherence tomography" vol. 28, No. 21, Optics Letters—Nov. 2003, pp. 1-3.*
(Continued)

*Primary Examiner* — Mia M Thomas
(74) *Attorney, Agent, or Firm* — Sughrue Mion, PLLC

(57) ABSTRACT

An ophthalmic analysis apparatus is the ophthalmic analysis apparatus for obtaining analysis results of tomography images of a subject eye acquired at different dates by ophthalmic optical coherence tomography and outputting statistical information formed based on time-series data of the analysis results, and includes instruction receiving means for receiving selection instructions to select an analytical region on a subject eye from an examiner, and control means for respectively acquiring analysis results in the analytical region selected by the instruction receiving means with respect to tomography images acquired at the different dates and outputting the statistical information.

18 Claims, 10 Drawing Sheets

(51) Int. Cl.
*A61B 3/10* (2006.01)
*G06F 19/00* (2018.01)

(56) References Cited

U.S. PATENT DOCUMENTS

| | | | |
|---|---|---|---|
| 8,251,510 B2 | 8/2012 | Kobayashi et al. | |
| 8,801,187 B1* | 8/2014 | Knighton | A61B 3/102 345/418 |
| 9,326,679 B2* | 5/2016 | Takai | A61B 3/102 |
| 2002/0077755 A1* | 6/2002 | Hirai | G06F 19/3443 702/19 |
| 2002/0186818 A1* | 12/2002 | Arnaud | A61B 6/583 378/165 |
| 2005/0214222 A1* | 9/2005 | McKinnon | A61K 49/001 424/9.6 |
| 2005/0254721 A1* | 11/2005 | Hagiwara | G06T 5/008 382/260 |
| 2006/0093199 A1* | 5/2006 | Fram | A61B 6/5223 382/128 |
| 2006/0159319 A1* | 7/2006 | Sathyanarayana | G06K 9/00 382/128 |
| 2006/0184050 A1* | 8/2006 | Urano | A61B 5/0062 600/485 |
| 2006/0210121 A1* | 9/2006 | Nakano | G06K 9/0061 382/117 |
| 2006/0274269 A1* | 12/2006 | Koest | A61B 3/117 351/246 |
| 2006/0274928 A1* | 12/2006 | Collins | A61B 6/00 382/132 |
| 2007/0133852 A1* | 6/2007 | Collins | A61B 8/08 382/128 |
| 2007/0195269 A1* | 8/2007 | Wei | A61B 3/102 351/221 |
| 2007/0263227 A1* | 11/2007 | Mujat | A61B 3/102 356/511 |
| 2008/0058617 A1* | 3/2008 | Hwang | A61B 5/4872 600/310 |
| 2008/0090199 A1* | 4/2008 | Noguchi | A61B 5/0088 433/29 |
| 2008/0100612 A1 | 5/2008 | Dastmalchi et al. | |
| 2008/0137034 A1* | 6/2008 | Wernick | A61B 3/1216 351/221 |
| 2008/0152204 A1* | 6/2008 | Huo | G06K 9/2054 382/132 |
| 2008/0169808 A1* | 7/2008 | Taniguchi | G01R 33/4824 324/307 |
| 2008/0201350 A1* | 8/2008 | Thattil | G06F 17/30528 |
| 2008/0221834 A1* | 9/2008 | Damodharan | G06F 11/2257 702/183 |
| 2008/0231272 A1* | 9/2008 | Taniguchi | G01R 33/4818 324/309 |
| 2008/0240581 A1* | 10/2008 | Napoletani | G06K 9/6229 382/224 |
| 2008/0249430 A1* | 10/2008 | John | A61B 5/0476 600/544 |
| 2008/0312552 A1 | 12/2008 | Zhou et al. | |
| 2009/0022265 A1* | 1/2009 | Takase | A61B 6/469 378/8 |
| 2009/0079937 A1* | 3/2009 | Chen | A61B 3/0008 351/210 |
| 2009/0123036 A1* | 5/2009 | Huang | A61B 3/0058 382/117 |
| 2009/0123044 A1* | 5/2009 | Huang | A61B 3/0033 382/128 |
| 2010/0002152 A1* | 1/2010 | Nishioka | G09G 3/02 348/744 |
| 2010/0110172 A1* | 5/2010 | Satake | A61B 3/102 348/78 |
| 2010/0118369 A1* | 5/2010 | Takayama | G02B 26/101 359/213.1 |
| 2010/0128841 A1* | 5/2010 | Imas | G06T 5/50 378/16 |
| 2010/0238403 A1 | 9/2010 | Kobayashi et al. | |
| 2011/0002516 A1* | 1/2011 | Manri | G01N 15/147 382/128 |
| 2011/0007957 A1* | 1/2011 | Sakagawa | A61B 3/102 382/131 |
| 2011/0109764 A1* | 5/2011 | Hong | G02B 7/36 348/222.1 |
| 2011/0129133 A1 | 6/2011 | Ramos et al. | |
| 2011/0176716 A1 | 7/2011 | Kim et al. | |
| 2011/0194738 A1* | 8/2011 | Choi | G06K 9/0061 382/117 |
| 2011/0218439 A1* | 9/2011 | Masui | A61B 8/08 600/443 |
| 2011/0243415 A1* | 10/2011 | Yonezawa | G06T 7/0012 382/131 |
| 2011/0267340 A1* | 11/2011 | Kraus | A61B 3/102 345/419 |
| 2011/0268338 A1 | 11/2011 | Collins et al. | |
| 2011/0275931 A1* | 11/2011 | Debuc | A61B 3/102 600/425 |
| 2012/0007839 A1* | 1/2012 | Tsao | G02B 26/00 345/204 |
| 2012/0026304 A1* | 2/2012 | Kawahara | H04N 13/0438 348/55 |
| 2012/0035480 A1* | 2/2012 | Migita | A61B 8/5269 600/443 |
| 2012/0054230 A1* | 3/2012 | Kanada | G16H 15/00 707/769 |
| 2012/0095439 A1 | 4/2012 | de Juan, Jr. et al. | |
| 2012/0133733 A1* | 5/2012 | Sakaniwa | H04N 13/0025 348/43 |
| 2012/0170027 A1* | 7/2012 | Tsukizawa | G06T 1/00 356/124 |
| 2012/0177262 A1* | 7/2012 | Bhuiyan | G06T 7/0046 382/128 |
| 2012/0184845 A1 | 7/2012 | Ishikawa et al. | |
| 2012/0230553 A1* | 9/2012 | Chandra Bijalwan | G06K 9/00604 382/117 |
| 2013/0093995 A1* | 4/2013 | Suehira | A61B 3/14 351/206 |
| 2013/0172731 A1* | 7/2013 | Gole | A61B 5/0035 600/424 |
| 2013/0182895 A1* | 7/2013 | Touzov | G06F 19/321 382/103 |
| 2013/0208240 A1* | 8/2013 | Sharma | A61B 3/102 351/206 |
| 2013/0236088 A1* | 9/2013 | Umehara | G06T 7/001 382/149 |
| 2014/0163368 A1* | 6/2014 | Rousso | A61B 6/037 600/436 |
| 2014/0205169 A1* | 7/2014 | Yamakawa | G06T 7/0012 382/131 |
| 2015/0116663 A1* | 4/2015 | Kushida | A61B 3/00 351/206 |
| 2016/0055319 A1* | 2/2016 | Ikegaya | G06F 19/328 705/3 |

FOREIGN PATENT DOCUMENTS

| | | |
|---|---|---|
| JP | 2004-13509 A | 1/2004 |
| JP | 2005-237825 A | 9/2005 |
| JP | 2008-234272 A | 10/2008 |
| JP | 2009-516551 A | 4/2009 |
| JP | 2010-220771 A | 10/2010 |
| JP | 2010-246904 A | 11/2010 |
| JP | 2011-212232 A | 10/2011 |
| JP | 2012-48395 A | 3/2012 |
| JP | 2012-48636 A | 3/2012 |

OTHER PUBLICATIONS

Bo et al. "Signal-to-Noise Ratio Enhanced Spectral Domain Optical Coherence Tomography with Dual-Balanced Detection" Procedia Engineering 140 (2016) pp. 140-143.*

(56) References Cited

OTHER PUBLICATIONS

Extended European Search Report dated Mar. 24, 2014 issued by the European Patent Office in counterpart European Patent Application No. 13189919.7.
Office Action dated Mar. 14, 2017 by the Japanese Intellectual Property Office in counterpart Japanese Patent Application No. 2012-235206.
Communication issued by the Japanese Patent Office dated Jul. 25, 2017 in counterpart Japanese Patent Application No. 2012-235208.
Communication dated Feb. 21, 2018, from the Japanese Patent Office in counterpart application No. 2012-235207.
Office Action dated Jun. 19, 2018 by the Japanese Patent Office in counterpart Japanese Patent Application No. 2017-114913.

* cited by examiner

OPHTHALMIC ANALYSIS APPARATUS AND OPHTHALMIC ANALYSIS PROGRAM

CROSS-REFERENCE TO RELATED APPLICATION

This application is based upon and claims the benefit of priorities of Japanese Patent Application No. 2012-235206 filed on Oct. 24, 2012, Japanese Patent Application No. 2012-235207 filed on Oct. 24, 2012, and Japanese Patent Application No. 2012-235208 filed on Oct. 24, 2012, the contents of which are incorporated herein by reference in their entireties.

BACKGROUND

The present disclosure relates to an ophthalmic analysis apparatus and program for analyzing a subject eye.

There are cases where images in the same region of a subject eye are acquired at different examination dates by ophthalmic optical coherence tomography (OCT) and follow-up observations are made. For example, in the case of fundus OCT, tomography images of a fundus are acquired plural times and follow-up observations of a lesion are made based on a change in the tomography images (see JP-A-2010-246904).

SUMMARY

In the case of a disease of the eye, follow-up observations may be made over a very long span (for example, glaucoma or macular disease of fundus). Then, an analysis apparatus and an analysis program which are easy for an examiner to use and can easily check analysis results in the long-term follow-up observations are desired. For example, a result of trend analysis in the long-term follow-up observations was only one result using the whole data. Further, conventionally, long-term follow-up observations could be made for only a limited photographic pattern and an analyzable data region was preset.

A technical problem of an aspect of the present disclosure is to provide an ophthalmic analysis apparatus capable of suitably making long-term follow-up observations.

In order to solve the problem described above, the aspect of the present disclosure is characterized by including the following configuration.

(1) An ophthalmic analysis apparatus comprising:
    a processor; and
    memory for storing computer readable instructions, when executed by the processor, causing the ophthalmic analysis apparatus to function as:
        an obtaining unit configured to obtain analysis results of tomography images of a subject eye acquired at different dates by ophthalmic optical coherence tomography;
        an instruction receiving unit configured to receive, from an examiner, selection instructions to select an analytical region on the eye; and
        a generating unit configured to respectively acquire analysis results in the analytical region selected by the instruction receiving means with respect to tomography images acquired at the different dates and generate statistical information formed based on time-series data of the acquired analysis result; and
        an output unit configured to output the statistical information.

(2) The ophthalmic analysis apparatus according to (1), wherein the instruction receiving unit receives, from the examiner, selection instructions for a two-dimensional image at an examination date at which an analysis result is acquired.

(3) The ophthalmic analysis apparatus according to (2), wherein the two-dimensional image includes at least any of a tomography image, a front image, an analysis chart and an analysis map.

(4) The ophthalmic analysis apparatus according to (1), wherein
    the instruction receiving unit receives, from the examiner, selection instructions to select a one-dimensional region on the tomography image outputted to display unit, and
    the generating unit acquires at least one analysis result in the selected one-dimensional region.

(5) The ophthalmic analysis apparatus according to (1), wherein
    the instruction receiving unit receives, from the examiner, selection instructions to select a two-dimensional region on the tomography image outputted to a display screen of a display unit, and
    the generating unit acquires at least one analysis result in the selected two-dimensional region.

(6) The ophthalmic analysis apparatus according to (1), wherein the instruction receiving unit receives, from the examiner, selection instructions to select at least one section divided by an analysis chart indicating a fundamental statistic of an analysis result every preset section.

(7) An ophthalmic analysis apparatus comprising:
    a processor; and
    memory for storing computer readable instruction, when executed by the processor, causing the ophthalmic analysis apparatus to function as:
        an obtaining unit configured to obtain analysis results of tomography images of a subject eye acquired at different dates by ophthalmic optical coherence tomography;
        a generating unit configured to generate statistical information based on the time-series data of the acquired analysis result;
        an event receiving unit configured to receive an input of occurrence time of an event related to an eye disease of a subject and a name of the event, and
        a controller configured to add, to the statistical information, information indicating occurrence of the event in a position corresponding to the occurrence time received by the event receiving unit, and to output image data including the statistical information to which the information indicating occurrence of the event is added and a name of the event received by the event information receiving unit.

(8) The ophthalmic analysis apparatus according to (7), wherein the generating unit conducts a first regression analysis for conducting a regression analysis of the time-series data before the occurrence time and conducts a second regression analysis for conducting a regression analysis of the time-series data after the event occurrence time based on the occurrence time received by the event receiving unit, and outputs a trend graph including a first trend graph by the first regression analysis and a second trend graph by the second regression analysis as the statistical information.

(9). The ophthalmic analysis apparatus according to (7), wherein the controller assigns and outputs elapsed time from an examination date or the occurrence time to a region in which a time axis in the time-series graph is represented.

(10) The ophthalmic analysis apparatus according to (7), wherein the generating unit conducts a first regression analysis for conducting a regression analysis of the time-series data before the occurrence time and conducts a second regression analysis for conducting a regression analysis of the time-series data after the event occurrence time based on the occurrence time received by the event receiving unit, and displays a slope by the first regression analysis and a slope by the second regression analysis so that the slope by the first regression analysis can be compared with the slope by the second regression analysis.

(11) The ophthalmic analysis apparatus according to (7), wherein the controller displays the time-series graph of the eye and a normal eye time-series graph formed based on time-series data of a normal eye so that the time-series graph of the eye can be compared with the normal eye time-series graph.

(12) The ophthalmic analysis apparatus according to (7), wherein the controller outputs positional information indicating a position on a fundus of an analysis result outputted to the time-series graph together with the time-series graph.

(13) The ophthalmic analysis apparatus according to (7), wherein the controller outputs another time-series graph including time-series data of an analysis result obtained by another ophthalmic apparatus different from optical coherence tomography for fundus photograph together with the time-series graph.

(14) An ophthalmic analysis apparatus comprising:
  a processor; and
  memory for storing computer readable instruction, when executed by the processor, causing the ophthalmic analysis apparatus to function as:
    an obtaining unit configured to obtain analysis results of tomography images of a subject eye acquired at different dates by ophthalmic optical coherence tomography;
    a generating unit configured to generate statistical information based on the time-series data of the acquired analysis result;
    an instruction receiving unit configured to receive, from an examiner, selection instructions to select plural two-dimensional images outputted as plural two-dimensional images at each examination date for a specific period on the statistical information; and
    a controller configured to output an image data in which the plural two-dimensional images selected by the instruction receiving unit are arranged together with the statistical information.

(15) The ophthalmic analysis apparatus according to (14), wherein the instruction receiving unit receives, from the examiner, change instructions to change a two-dimensional image displayed on a display unit, and the controller changes the two-dimensional image displayed on the display unit according to change instructions from the instruction receiving unit.

(16) The ophthalmic analysis apparatus according to (15), wherein the instruction receiving unit receives, from the examiner, the selection instructions to select at least one of the two-dimensional images displayed on the display unit as a fixed display image, and the controller changes and displays another two-dimensional image different from the fixed image according to change instructions from the instruction receiving unit while fixing display of a two-dimensional image selected as the fixed display image.

(17) A computer readable recording medium storing computer readable computer readable instructions, when executed by the processor, causing an ophthalmic analysis apparatus to function as:
  an obtaining unit configured to obtain analysis results of tomography images of a subject eye acquired at different dates by ophthalmic optical coherence tomography;
  an instruction receiving unit configured to receive, from an examiner, selection instructions to select an analytical region on the eye; and
  a controller configured to respectively acquire analysis results in the analytical region selected by the instruction receiving unit with respect to tomography images acquired at the different dates and generate statistical information formed based on time-series data of the acquired analysis result; and
  an output unit configured to output the generated statistical information.

According to the aspect of the preset disclosure, long-term follow-up observations can be made suitably.

DESCRIPTION OF EXEMPLARY EMBODIMENTS

Figure 1:
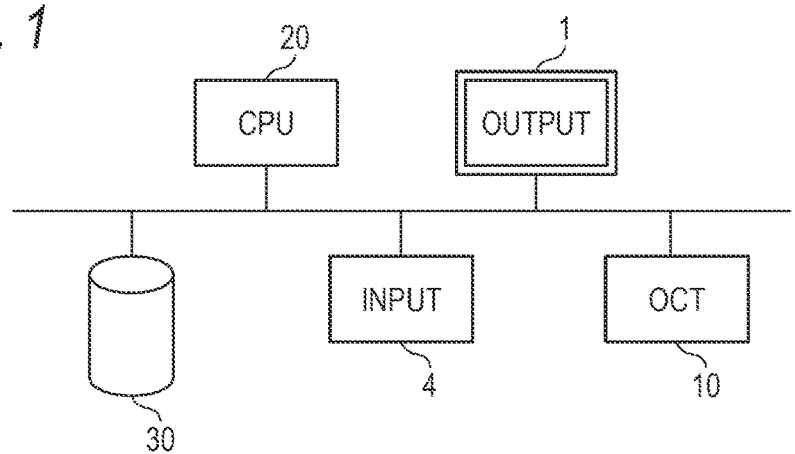
FIG. 1 is a block diagram showing a configuration of an ophthalmic analysis apparatus according to an example.
Figure 2:
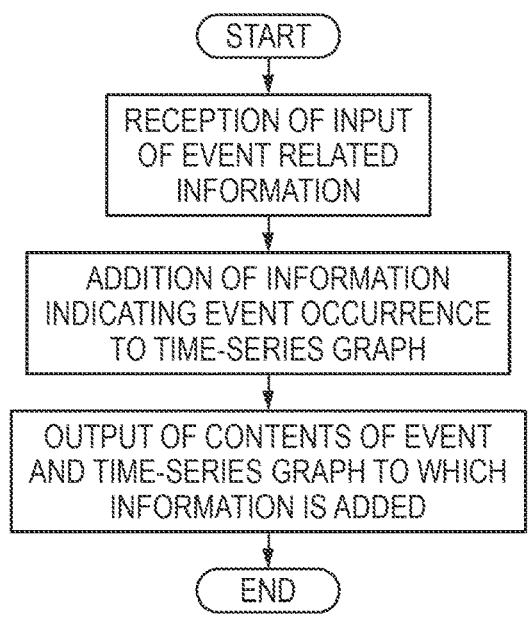
FIG. 2 is a flowchart showing one example of assignment of event information.
Figure 3:
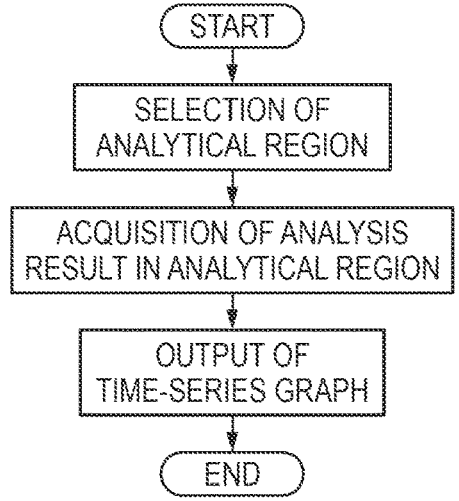
FIG. 3 is a diagram showing one example in the case of outputting a time-series graph in an analytical region selected by an examiner.

An exemplary embodiment of the present disclosure will be described based on the drawings. FIGS. 1 to 13 are diagrams according to an example of the present embodiment. In addition, items classified by the following brackets < > can be used independently or relationally.

<Outline>

An ophthalmic analysis apparatus obtains analysis results of tomography images of a subject eye acquired at different dates by optical coherence tomography (for example, optical coherence tomography 10), and outputs statistical information formed based on time-series data of the obtained analysis results.

In addition, as the analysis results, either analysis results of fundus tomography images or analysis results of anterior eye tomography images are applied. For example, the analysis results may be analysis results of tomography images of the whole eye ranging from a cornea to a fundus.

As the analysis results, for example, a thickness of the eye (for example, a thickness of at least one of a cornea, a crystalline lens, a retina layer and a choroid layer), a curvature of the eye (for example, a curvature of at least one of a cornea, anterior and posterior surfaces of a crystalline lens and a retina layer), etc. are acquired. In addition, the analysis results are outputted as information about, for example, an analytical value (for example, numerical data of thickness/curvature or an analytical parameter value of a ratio of C (cup) to D (disk) of a fundus optic nerve head), a measured value of an anterior chamber angle (for example, ACD, TISA or ANGLE) or lesion measurement information (for example, at least any of size, area and volume). Further, the analysis results may be evaluation values (for example, evaluation of six grades of A to F) obtained by stepwise classifying an analytical value. In addition, for example, for size of a lesion, a lesion region may be detected by image processing to measure any of size, area and volume of the lesion to form statistical data.

An instruction receiver (for example, a CPU 20) has a function of receiving selection instructions from an examiner. The instruction receiver can receive an operation signal from a user interface (an operation input unit) such as a touch panel, a mouse and a keyboard.

An input receiver (for example, the CPU 20) has a function of receiving an input from an examiner or one configuration of the apparatus. For example, the input receiver can receive an operation signal from an input unit 4 (for example, the user interface such as the touch panel, the mouse and the keyboard). For example, the input receiver can receive data from a storage unit for storing various pieces of information.

A controller (for example, the CPU 20) outputs a time-series graph. For example, an output destination (output unit) can include a display unit (for example, a display unit 1), an output device such as a printer, and a storage unit (a storage device) such as a hard disk or a USB memory. For the display unit, the time-series graph is displayed on a monitor, and for the printer, the time-series graph is printed. For the storage unit, the time-series graph stored in the storage unit is in a state capable of being outputted to the output device.

For example, when image data including the time-series graph is stored in the storage unit, the controller can output the image data from the storage unit to the output device and thus, this is advantageous.

As a device of the output destination, for example, at least any of a configuration mounted in the optical coherence tomography, a configuration externally attached to the optical coherence tomography and a configuration arranged in a position separate from the optical coherence tomography can be used.

The storage unit may be, for example, a storage unit formed in an apparatus body of an OCT device, a storage unit formed in an external server or a storage unit formed in a personal computer. Of course, the storage unit for storing a fundus analysis program, the storage unit for storing each analysis result and the storage unit for storing statistical information may respectively have separate configurations. Of course, the storage units may have the same configuration.

The controller (for example, the CPU 20) may acquire time-series data of analysis results from a storage unit (for example, a storage unit 30) for storing analysis results of tomography images of the eye acquired at different dates and output a time-series graph including the time-series data.

Data outputted by the controller is not limited to the time-series graph, and could be statistical information (for example, a numerical value or a chart) formed from the time-series data of the analysis results. The statistical information could be a statistical result in which distribution of the analysis results is collected in time sequence and characteristics of the time-series data can be grasped. As the statistical information, the statistical result is preferably represented by a numerical value or a chart. However, the following description is made focused on the time-series graph as one piece of statistical information, but can also be applied to other statistical information.

<Trend Graph (See FIGS. 4 to 8)>

The controller may, for example, acquire a regression line by conducting a regression analysis of time-series data and also output a trend graph by the regression line as a time-series graph. For example, the controller may output a p value or a slope of the acquired regression line. In addition, the controller may acquire a regression curve by a regression analysis and output a trend graph by the regression curve.

<Assignment of Event Information (See Flowchart of FIG. 2 and Graphs of FIGS. 4, 6 and 8)>

For example, the input receiver may receive an input of an event name and occurrence time of an event related to an eye disease of a subject. For example, the controller may add information indicating occurrence of an event to a position corresponding to the occurrence time received by the input receiver in a time-series graph. For example, the controller may output image data including the time-series graph to which the information indicating occurrence of the event is added and the event name received by the input receiver to an output destination.

Accordingly, an examiner can associate the event with the transition of analysis results since event information about the eye disease of the subject is assigned to the time-series graph.

For example, the input receiver may obtain the event-related information as described above from a manual input of the examiner. For example, the input receiver may obtain the event-related information as described above from data of an electronic medical record.

The occurrence time of the event may be, for example, information indicating the time of the occurrence of the event. It is preferable to be the date (year, month and day) of the occurrence of the event. For long-term treatment of the eye disease, only the date (year and month) may be sufficient. For short-term treatment of the eye disease, only the date (month and day) may be sufficient. The occurrence time of the event is not limited to these, and includes information about the age (for example, years and months) of the subject at the time of the occurrence of the event, an elapsed period from the examination date (for example, the time of first medical examination or re-examination) to the event, etc.

The event name may be, for example, names indicating events of medication to the subject, surgery on the subject, a check of a symptom of the subject, etc. Concretely, the event name may be information about a concrete name (for example, a product name) of a drug on medication, a concrete name (for example, laser photocoagulation surgery) of surgery, a concrete name (for example, a check of age-related macular degeneration) of a checked symptom, etc. In addition, a name of an event related to medication includes the start of medication, the end of medication, a change in medication, etc.

For example, the controller may add the event name to a time-series graph. For example, the controller may assign information indicating the occurrence of the event to the time-series graph and output the event name to the outside of the graph.

<Creation of Trend Graph Based on Time of Event Occurrence>

For example, the controller may acquire a first regression line by conducting a regression analysis of time-series data before occurrence time based on the occurrence time received by the input receiver. For example, the controller may acquire a second regression line by conducting a regression analysis of time-series data after event occurrence time. For example, the controller may output a trend graph including at least any of a first trend graph by the first regression line and a second trend graph by the second regression line as a time-series graph. In addition, the controller may acquire a regression curve by a regression analysis and output a trend graph by the regression curve.

In the case of creating each of the trend graphs before and after the occurrence time, the controller may create the trend graph including analysis results obtained at the event occurrence time or create the trend graph without including the analysis results obtained at the event occurrence time.

<Slope Comparison Based on Time of Event Occurrence>

The controller may display a first slope by the first regression analysis described above and a second slope by the second regression analysis described above (see FIG. 8) so that the first slope can be compared with the second slope.

In the case of producing an output for comparison, for example, the controller may display the first slope and the second slope on the same screen or display the first slope and the second slope in parallel.

<Assignment of Elapsed Time from Event Occurrence Time>

For example, the controller may assign elapsed time from occurrence time or an examination date to a region of notation of the time axis in a time-series graph and output the elapsed time. For example, by assigning the elapsed time from the event occurrence, an examiner can easily check a relation between a lapse of time and a change in analysis results after the event occurrence. Also, by assigning the elapsed time from any examination date (for example, the first date of examination), the examiner can easily check a relation between a lapse of time and a change in analysis results after any examination date.

<Comparison with Normal Eye Graph>

For example, the controller may output a time-series graph (first graph) of the eye and a time-series graph (second graph) of a normal eye formed based on time-series data of the normal eye so that the first graph can be compared with the second graph. Accordingly, a temporal change (change over time) in analysis results of the eye can easily be compared with a temporal change in the normal eye.

In the case of producing an output for comparison, for example, the controller may display the first graph and the second graph on the same graph or display the first graph and the second graph in parallel.

<Comparison Between Slope of Trend Graph Slope of Normal Eye>

For example, the controller may compare a slope of a first regression line acquired by conducting a regression analysis of time-series data of the eye with a slope of a second regression line acquired by conducting a regression analysis of time-series data of normal eye data, and output a comparison result. Accordingly, a temporal change in analysis results of the eye can easily be compared with a temporal change in the normal eye.

In the case of producing an output for comparison, for example, the controller output the slope of the first regression line and the slope of the second regression line simultaneously. For example, the controller may output a state as to whether the slope of the first regression line is larger or smaller than the slope of the second regression line.

<Output of Positional Information Indicating Position on Fundus of Data Outputted on Graph (See FIGS. 4, 6 and 8)>

For example, the controller may output positional information indicating a position on the eye of analysis results outputted to a time-series graph together with the time-series graph. Accordingly, an examiner can easily check the position on a fundus of the analysis results. The positional information may be, for example, information (for example, any of a cornea, a crystalline lens and the fundus) indicating an analysis region in the eye or positional information (for example, two-dimensional positional information on the fundus) on a predetermined region of the eye.

<Discrimination Display of Graph Output Position>

For example, the controller may use a diagram or a table in the case of outputting positional information indicating a position on the eye. Further, for example, the controller may produce an output discriminably by outputting the portion which is not outputted on a time-series graph and the portion outputted on the time-series graph in the diagram or the table in different display modes.

In the case of producing an output discriminably, for example, the controller colors a section outputted on the graph in a chart sectioned according to a fundus position. In addition to coloring, the section may be hatched or a frame may be formed in the section. The section outputted on the time-series graph may be highlighted.

When a graph about plural analytical regions is outputted on the graph, an output may be produced discriminably by outputting each of the analytical regions in the diagram or the table in different modes.

<Custom Graph (See FIGS. 5 and 7)>

For example, the controller may output another time-series graph including time-series data of measured results obtained by another ophthalmic apparatus different from optical coherence tomography for fundus photography together with the time-series graph. The measured results obtained by another ophthalmic apparatus include eyesight, an MD value, a VFI (Visual Field Index) value, a TD (Total deviation) value, a PSD value (Pattern Standard deviation), spectral luminous sensitivity (ERG, MP, etc.), a blood flow, size or volume of a focus of disease (for example, edema or leak), etc. A custom graph is not limited to one.

<Setting of any Follow-Up Observation Position (See Flowchart of FIG. 3)>

The instruction receiver may receive selection instructions to select at least one of the analytical regions in plural positions of the eye as a graph creation region of a time-series graph from an examiner. The plural positions of the eye may be, for example, plural positions (for example, any of a cornea, a crystalline lens and a fundus) of the whole eye, or plural positions (for example, two-dimensional positional information on the fundus) on a predetermined region of the eye.

The controller respectively acquires analysis results in the analytical region selected by the selection instructions received by the instruction receiver with respect to tomography images acquired at different dates, and outputs a time-series graph to an output destination. The time-series graph could be a graph for representing a temporal change in analysis results of the eye to the tomography images, and, for example, a graph for plotting each of the analysis results in time sequence, a trend graph by trend analysis of each of the analysis results, etc. are outputted.

Accordingly, an examiner can easily check a temporal change in analysis results of a region of interest to the examiner since the time-series graph in a region selected by the examiner is outputted.

In the case of receiving the selection instructions to select the analytical region from the examiner, the controller may, for example, receive selection instructions from the examiner with respect to a two-dimensional image at the examination date at which analysis results are acquired. The two-dimensional image may be, for example, at least any of a two-dimensional tomography image, a two-dimensional front image (may be a front image generated from an interference signal of OCT in addition to a fundus camera image and SLO), a two-dimensional analysis chart and a two-dimensional analysis map. Of course, the examiner may receive selection instructions from the examiner with respect to a three-dimensional image at the examination date at which analysis results are acquired.

For example, the instruction receiver may receive selection instructions from the examiner on a display screen outputted to the display unit. A tomography image, a front image, an analysis chart and an analysis map on the display screen are used for selecting a graph creation region.

In the case of acquiring analysis results of the region selected as the graph creation region, for example, the controller can reduce processing time by acquiring analysis results previously acquired in the selected region. Of course, when the graph creation region is selected, for example, the controller may analyze a tomography image and acquire analysis results in the selected region.

<Setting of Follow-Up Observation Position on Tomography Image (See FIGS. 11 to 13)>

For example, the instruction receiver may receive selection instructions to select at least a part on a tomography image as a graph creation region from an examiner. For example, the controller may respectively acquire analysis results in an analytical region selected on the tomography image with respect to tomography images acquired at different dates, and output a time-series graph to an output destination. Accordingly, the examiner can check a temporal change in analysis results of a region on the tomography image of interest to the examiner since the time-series graph in a region selected on the tomography image is outputted.

For example, the controller may acquire analysis results in a selected analytical region with respect to a tomography image used for selection instructions, and also obtain analysis results of the same region as the selected analytical region with respect to other tomography images acquired at different dates. For example, in the case of obtaining analysis results of the same region, the controller may acquire analysis results associated with a coordinate position at the same region on other tomography images when analysis results associated with a coordinate position on the tomography image selected as the analytical region are acquired.

The coordinate position of the tomography image may be previously associated with analysis results in the coordinate position. In the case of obtaining analysis results acquired previously, for example, the controller may obtain analysis results corresponding to the coordinate position specified when the coordinate position of the tomography image corresponding to the selected analytical region is specified.

In the case of obtaining analysis results of the same region at different dates, the controller preferably has tomography images with matching scan patterns of OCT, but it is not limited to this. For example, even for different scan patterns, a photography region has only to be common. Also, plural tomography images acquired at different dates are preferably at least three or more tomography images.

As a region selected by the instruction receiver, for example, a one-dimensional region (see FIG. 12) or a two-dimensional region (see FIG. 13) on a tomography image can be selected. As the one-dimensional region, for example, an analysis result in a depth direction is selected by setting one line in the depth direction. Of course, at least a part of the line in other directions (for example, a transverse line) may be selected. The line does not have to be a line extending from one end to the other end of the image, and may be a part of the line.

As the two-dimensional region, for example, analysis results in a depth direction in plural positions may be selected by setting a region including plural A scan lines in the depth direction. The A scan line does not have to be an A scan line extending from one end to the other end of the image, and may be a part of the A scan line. The same applies to a region set in a transverse direction.

In the case of setting a follow-up observation position in a one-dimensional region on a tomography image, for example, the instruction receiver may receive selection instructions to select the one-dimensional region on the tomography image outputted to a display screen of the display unit as a graph creation region from an examiner. For example, the controller may acquire at least one analysis result in the selected one-dimensional region. Accordingly, a time-series graph in the one-dimensional region on the tomography image selected by the examiner is outputted.

For example, a line (a straight line, a segment) movable on a tomography image is superimposed and displayed, and a one-dimensional region specified by the line is selected as a graph creation region. The region is not limited to this, and the selected one-dimensional region could be displayed discriminably by being displayed in a display mode different from other regions. For example, the selected one-dimensional region may be displayed in different display modes (for example, different colors or different contrasts). It may be configured to receive specification of any two points on the tomography image and select a region connecting the two points.

In the case of setting a follow-up observation position in a two-dimensional region on a tomography image, for example, the instruction receiver may receive selection instructions to select the two-dimensional region on the tomography image outputted to a display screen of the display unit as a graph creation region from an examiner. For example, the controller may acquire at least one analysis result in the selected two-dimensional region. Accordingly, a time-series graph in the two-dimensional region on the tomography image selected by the examiner is outputted.

For example, a frame movable on a tomography image is superimposed and displayed, and a two-dimensional region specified by the frame is selected as a graph creation region. A shape of the frame is not limited to a rectangle, and any shapes (for example, a circle) are used. The region is not limited to this, and the selected two-dimensional region could be displayed discriminably from other regions. For example, the selected two-dimensional region may be displayed in different display modes (for example, different colors or different contrasts).

It may be configured to receive specification of any two points on the tomography image and select a two-dimensional region using a segment connecting the two points as a diagonal line as an analytical region.

In the case of acquiring at least one analysis result in the two-dimensional region, for example, the controller may obtain an analysis result obtained by integrating plural analysis results. As the integrated result, a fundamental statistic may be used. The fundamental statistic may be representative values (a mean value, a median value, a mode value, a maximum value, a minimum value, etc.), degree of scattering (variance, standard deviation or a variation coefficient), etc.

Concretely, the controller may acquire a representative value (for example, a mean value) of analysis results every A scan signal in the two-dimensional region, or acquire a maximum value or a minimum value in analysis results every A scan signal in the two-dimensional region.

<Setting of Follow-Up Observation Position on Analysis Chart (See Analytical Region Display 170 of FIGS. 4, 6 and 8)>

For example, the instruction receiver may receive selection instructions to select at least one section divided by an analysis chart (for example, a fundus analysis chart or an anterior eye analysis chart) as a graph creation region from an examiner. For example, the controller may respectively acquire analysis results in the section selected as the graph creation region with respect to tomography images acquired at different dates, and output a time-series graph to an output destination. Accordingly, the time-series graph indicating a temporal change in analysis results of the section divided by the analysis chart is outputted. The examiner can check a temporal change in analysis results of the analysis chart.

In the analysis chart (see an analysis chart 130 of FIG. 4), for example, the controller shows an analytical value every preset section. The controller may obtain a fundamental statistic of analysis results every preset section as the analytical value. The fundamental statistic may be representative values (a mean value, a median value, a mode value, a maximum value, a minimum value, etc.), degree of scattering (variance, standard deviation or a variation coefficient), etc.

More concretely, the analysis chart may be a chart indicating representative values (for example, a mean value or a median value) of analysis results every preset section. The analysis chart may be a chart indicating a maximum value or a minimum value of analysis results every preset section. Analysis results in each position of the inside of the section are included in the analysis results every section to thereby obtain a stable analytical value.

The analysis chart is displayed on, for example, the display unit. For example, when an examiner selects at least one section from graphics simulating the analysis chart, the instruction receiver may be configured to receive selection instructions from the examiner. For example, when an examiner selects a section of an analysis chart of the eye in which analysis results are displayed in a section unit, the instruction receiver may be configured to receive selection instructions from the examiner. According to the two examples described above, the examiner can easily select a desired section. Also, the examples are not limited to this, and, for example, when at least one section is selected in a display format in which each section is listed, the instruction receiver may be configured to receive selection instructions from the examiner.

The number of sections selected by the instruction receiver may be one or plurality. An analysis chart used for creating a time-series graph may be configured to be selected from plural analysis charts. Of course, the analysis chart may be a single analysis chart incapable of selection.

In the case of acquiring analysis results, for example, the controller may calculate the analysis results at a point in time of selecting a section. In the case of acquiring analysis results, for example, the controller may be configured to acquire analysis results corresponding to a section selected from an analysis chart previously having analysis results.

For example, the controller may obtain analysis results corresponding to the same section of the same chart based on tomography images acquired at different dates. Of course, the section may be other sections according to acquisition dates.

The analysis chart is calculated based on three-dimensional OCT data acquired by a two-dimensional scan (for example, a raster scan) on the eye. Of course, the analysis chart may be calculated based on each two-dimensional OCT data acquired by a multi-scan such as a radial scan.

<Display of Section Selective Region>

For example, the instruction receiver may output, to a display screen of the display unit, a section selector having a selective region formed in a position corresponding to each section of a chart. For example, the instruction receiver may receive section selection instructions from an examiner according to the selective region selected on the section selector. Accordingly, the examiner can easily check a time-series graph on at least a section of an analysis chart since the selective region every section is formed.

The section selector is, for example, graphics simulating the analysis chart, and the divided selective region may function as a selection button. The selective region is selected through, for example, touch panel operation or a click of a cursor.

<Output of Section Discrimination Information (See Graph 150a of FIGS. 4, 6 and 8)>

For example, the controller may discriminably output time-series graphs on plural sections in an analysis chart on the same graph. For example, the controller may output section discrimination information indicating a position on the analysis chart of the section outputted to the time-series graph. Accordingly an examiner can check the position on the analysis chart about the section displayed on the graph.

A discriminable output technique may be, for example, a technique for displaying a plot of a graph or a line connecting plots in different display modes (for example, different colors, different indexes or different line types).

The section discrimination information may be, for example, graphics having a display region formed in a position corresponding to each section of the analysis chart and indicating the section outputted to the time-series graph. The section discrimination information may be, for example, indexes or characters for identifying plural graphs.

In the case of outputting a time-series graph to a display screen of display means, the section discrimination information may be assigned to the section selective region described above. Accordingly, the examiner can easily check a section displayed on the graph and selection of the section since discrimination information and the selection of the section are displayed in the same region.

<Output of Two-Dimensional Image at Each Examination Date for Specific Period on Time-Series Graph (See FIG. 8)>

The instruction receiver (for example, the CPU 20) may receive selection instructions to select plural two-dimensional images, outputted to an output unit, at each examination date for a specific period within a period for which analysis results are outputted on a time-series graph from an examiner.

The controller (for example, the CPU 20) may output the plural two-dimensional images selected by the instruction receiver to the output unit in time sequence together with the time-series graph. Accordingly, the examiner can check the two-dimensional image about a period of interest on the time-series graph.

In the case of receiving selection instructions to select the plural two-dimensional images outputted to the output unit from the examiner, for example, the controller may receive the selection instructions from the examiner through a user interface.

For example, the instruction receiver may receive selection instructions from the examiner through operation (for example, scroll operation, scroll bar movement, drag operation, slide operation, flick operation, button movement or keyboard operation) with respect to a display region in which the two-dimensional images are displayed side by side.

For example, the instruction receiver may receive selection instructions from the examiner through operation (for example, click operation, scroll operation, scroll bar movement, drag operation, slide operation, flick operation, button movement or keyboard operation) with respect to a display region in which the time-series graph is displayed.

For example, the instruction receiver may receive selection instructions from the examiner through period input operation (for example, the start and the end of the period are inputted) through a user interface. The selection instructions from the examiner may be received by selection of a list.

The specific period may be, for example, a part of the whole period for which analysis results are outputted. The whole period may be the whole collection period of analysis results or a part of the whole collection period. In the case of the whole collection period, a part of the whole period may be specified, and in the case of a part of the whole collection period, a part of the period may be specified from among the part of the whole collection period.

The controller may output at least any of a photography image and an analysis image as the two-dimensional image. In the case of outputting the photography image, the controller may output a tomography image acquired by ophthalmic optical coherence tomography. Accordingly, the examiner can check the tomography image about a period of interest on the time-series graph. In this case, it is preferable to be the original tomography image in which analysis results outputted on the time-series graph are acquired, but a certain effect can be obtained even for other tomography images.

Also, the controller may output a front image (for example, a front image acquired by a fundus camera or SLO) acquired at the same date as the tomography image as the photography image. Accordingly, the examiner can check the front image about a period of interest on the time-series graph.

In the case of outputting the analysis image, the controller may output at least any of an analysis map, an analysis chart and an analysis result table. Accordingly, the examiner can check the analysis map or the analysis chart about a period of interest on the time-series graph. In this case, it is preferable to be the analysis map or the analysis chart including analysis results outputted on the time-series graph, but a certain effect can be obtained even for other tomography images.

For example, the controller may output a color map for two-dimensionally representing analysis results (for example, a thickness or a curvature of the eye) on the eye as the analysis map. For example, the controller may output a chart indicating a representative value of analysis results (for example, a thickness or a curvature of the eye) every preset section as the analysis chart. Also, the controller may output a papilla analysis result, a central thickness or a volume value as a table as the analysis result table.

<Change in Period for which Two-Dimensional Image is Outputted>

The instruction receiver may receive change instructions to change a specific period from an examiner, and the controller may change a two-dimensional image according to the specific period changed by the instruction receiver. Accordingly, the examiner can change a period of interest on a time-series graph and check the two-dimensional image for the changed period.

For example, the controller may output the two-dimensional images about the specific period changed by the instruction receiver so that the two-dimensional images are arranged side by side. The instruction receiver may receive change instructions from the examiner by operation similar to the selection instructions from the examiner described above.

<Fixed Display of Part of Two-Dimensional Image (See FIGS. 9A and 9B)>

The instruction receiver may receive selection instructions to select at least one two-dimensional image displayed on the display unit as a fixed display image from an examiner. The controller may change and display another two-dimensional image different from a fixed image according to change instructions from the instruction receiver while fixing display of the two-dimensional image selected as the fixed display image.

Accordingly, the examiner can easily compare an attention region with other regions beyond time-series order.

The instruction receiver may, for example, be configured to receive selection instructions to be selected as the fixed display image from the examiner according to selection operation of the examiner with respect to the two-dimensional image displayed on the display unit.

The instruction receiver may, for example, be configured to receive selection instructions to be selected as the fixed display image from the examiner according to selection operation of the examiner with respect to a time-series graph.

The controller may, for example, mutually adjacently display the two-dimensional images selected as the fixed display image and also display other two-dimensional images in time sequence in a display region different from the fixed display image. Of course, the two-dimensional images selected as the fixed display image may be separated and displayed.

In this case, it is unnecessary to display the fixed display image and other images in time sequence. The fixed display image and other images may be divided and displayed.

<Discrimination Display of Period for which Two-Dimensional Image is Outputted>

The controller may produce an output discriminably by outputting a specific period for which a two-dimensional image is outputted on a time-series graph in different display modes. An examiner can easily associate the two-dimensional image with the graph since the specific period for which the two-dimensional image is outputted can be discriminated on the time-series graph.

For example, in the case of producing an output discriminably, for example, the controller may output a graph on the specific period for which the two-dimensional image is outputted and graphs on other periods in different display modes. Concretely, the controller may output plots or lines of the specific period and other periods in different modes (for example, different colors, different line types, the presence or absence of filling, different animation (for example, one period is fixed and displayed, and the other period is blinked and displayed), etc.). The controller may highlight the graph on the specific period for which the two-dimensional image is outputted.

The controller may assign display indicating the specific period for which the two-dimensional image is outputted on the time-series graph.

In the case of producing an output discriminably, the controller may divide and output the specific period and another period on the time-series graph. Concretely, the controller may add a division line to a boundary between the specific period and another period as a division output. As the division line, for example, division by a line or division by outputting backgrounds of graphs of the specific period and another period in different modes (for example, different colors) may be used.

In the case of discriminably producing an output on a display screen on the display unit 1, the controller may display analysis results of the specific period in a first display mode and also display analysis results of another period in a second display mode different from the first display mode on the time-series graph.

In the case of displaying the time-series graph to which the division line described above is added on the display screen on the display unit 1, the instruction receiver may receive change instructions to change the specific period from the examiner according to movement of the division line movable on the time-series graph. The controller may arrange and display the two-dimensional image on the specific period corresponding to the moved division line.

<Selection of Specific Period Using Graph>

The controller may divide and display a specific period and another period in a time-series graph displayed on a display screen on the display unit. The instruction receiver may receive operation from an input unit for changing a display position of division display as change instructions from an examiner. The controller may change a two-dimensional image according to the specific period changed by the instruction receiver. Accordingly, the examiner can easily conduct a detailed analysis since the two-dimensional image of a desired period can be changed from the time-series graph.

<Program>

An analysis apparatus includes a processor (for example, a CPU) for performing various control processing, and a storage medium for storing an analysis program. The processor executes the processing according to the analysis program.

Embodiment

An embodiment of the present embodiment will hereinafter be described concretely along the drawings. In the following description, an ophthalmic analysis apparatus will be described by taking a fundus analysis apparatus as an embodiment.

The embodiment will hereinafter be described based on the drawings. FIG. 1 is a block diagram showing a configuration of the fundus analysis apparatus according to the embodiment. As shown in FIG. 1, the present apparatus is configured to include a CPU (Central Processing Unit) 20 as a processor for performing arithmetic processing of the whole fundus analysis apparatus, a storage unit 30, a display unit 1 and an input unit 4. Each of the units is electrically connected to the CPU 20 through a bus etc.

The storage unit 30 stores a fundus analysis program for follow-up observation, and is constructed of, for example, a hard disk or a flash memory.

As the CPU 20, the input unit 4, the storage unit 30 and the display unit 1, an arithmetic processing unit, an input unit, a storage unit and a display unit had by a commercial PC (personal computer) are used, and the fundus analysis program may be installed on the commercial PC. Of course, an arithmetic processing unit, an input unit, a storage unit and a display unit had by optical coherence tomography 10 may be used as the CPU 20, the input unit 4, the storage unit 30 and the display unit 1.

The display unit 1 displays tomography images obtained by ophthalmic optical coherence tomography, analysis results of the tomography images, a time-series graph formed based on time-series data of the obtained analysis results, etc. on a display screen. The input unit 4 is constructed of a keyboard, a mouse, etc., and has a configuration in which a user (user) of the fundus analysis apparatus inputs various pieces of information.

The fundus analysis apparatus of the present embodiment is, for example, a computer, and after the CPU 20 reads out the fundus analysis program described above on RAM, the CPU 20 executes the program by performing various arithmetic processing. For example, the CPU 20 controls the display screen of the display unit 1 according to the fundus analysis program.

Analysis results of tomography images of the eye acquired at different dates by the optical coherence tomography 10 are stored in the storage unit 30 of FIG. 1. For example, formation results every examination date every subject targeted for follow-up observation are included.

In addition to the analysis results, for example, the original tomography images for obtaining the analysis results, layer thickness map images (for example, thickness map images) based on the analysis results, scan patterns at the time of acquiring the tomography images, or scan positions may be stored in the storage unit 30. The data is properly converted into image data by the CPU 20 and is presented to a user through the display unit 1 on the screen.

For example, information related to an event may be stored in the storage unit 30. The information related to the event includes, for example, information related to an event about treatment for a retina. For example, the date of occurrence of an event or a kind of event (for example, medication, surgery (photocoagulation, TTT, PDT, etc.) etc.) may be stored every subject. The scheduled date of occurrence of a future event and a kind of its event may be stored in the storage unit 30.

For example, a normal eye database may be stored in the storage unit 30. For example, a database for storing a retina thickness of a normal eye about a retinal disease based on prescription results and examination results of multiple patient eyes may be stored in the normal eye database. The normal eye database makes a database, for example, in a state in which a disease is not specified and a thickness or a tilt of a retina is classified into normality and abnormality. Of course, the normal eye database may be formed every specific disease. Also, the normal eye database about myopia may be constructed.

The optical coherence tomography (OCT) 10 is an apparatus for obtaining a tomography image of a fundus of the eye, and an analysis result (for example, retina thickness information) of the fundus of the eye is acquired based on the acquired tomography image. In a function of analyzing the tomography image and obtaining the analysis result, a controller for controlling the optical coherence tomography (OCT) 10 may be configured to analyze the tomography image, or another controller may be configured to analyze the tomography image obtained by the optical coherence tomography (OCT) 10.

The optical coherence tomography 10 divides light emitted from a light source into measurement light and reference light. Then, the optical coherence tomography 10 guides the divided measurement light to a fundus Ef of an eye E, and guides the divided reference light to a reference optical system. Thereafter, interference light by synthesis of the reference light and the measurement light reflected by the fundus Ef is received by a detector (light receiving element). The detector detects a state of interference between the measurement light and the reference light. In the case of Fourier domain OCT, spectral intensity of the interference light is detected by the detector and a depth profile in a predetermined range is acquired by Fourier transformation to spectral intensity data. The Fourier domain OCT includes Spectral-DomainOCT (SD-OCT) or Swept-sourceOCT (SS-OCT). Also, the optical coherence tomography 10 may be Time-DomainOCT (TD-OCT).

The optical coherence tomography (OCT) 10 may be provided with a front observation optical system for obtaining a front image of the fundus of the eye. The front observation optical system includes a scanning confocal optical system or a fundus camera optical system. Also, it may be configured to acquire a fundus front image based on an interference signal acquired by the optical coherence tomography 10.

The optical coherence tomography 10 obtains a tomography image of the fundus Ef based on an output signal from the detector. For example, image processing of the acquired tomography image is performed and a retina thickness of the fundus Ef is measured. As the retina thickness, for example, thicknesses (concretely, a thickness of an optic nerve fiber layer (NFL), a thickness from a nerve fiber layer (NFL) to a retinal pigment epithelium (RPE), etc.) of each layer of a retina are acquired.

Of course, follow-up observations of two-dimensional retina thickness information (thickness map) may be made. The acquired retina thickness information is sent to the CPU 20 and is stored in the storage unit 30. Besides, various parameters, an analysis chart calculated based on thickness information, image information (for example, a tomography image or a front image of the eye E) obtained by the optical coherence tomography 10, etc. are stored in the storage unit 30.

A thickness of a choroid layer may be measured by processing the acquired tomography image. Of course, follow-up observations of two-dimensional choroid information (thickness map) may be made.

When examinations are periodically made by the optical coherence tomography 10, retina thickness information about different examination dates as results of follow-up observations is sent to the CPU 20 and then is stored in the storage unit 30. The retina thickness information stored in the storage unit 30 is, for example, associated with the time axis and is stored for follow-up observations. The retina thickness information using time as a function shows a temporal change in retina thickness.

Figure 4:
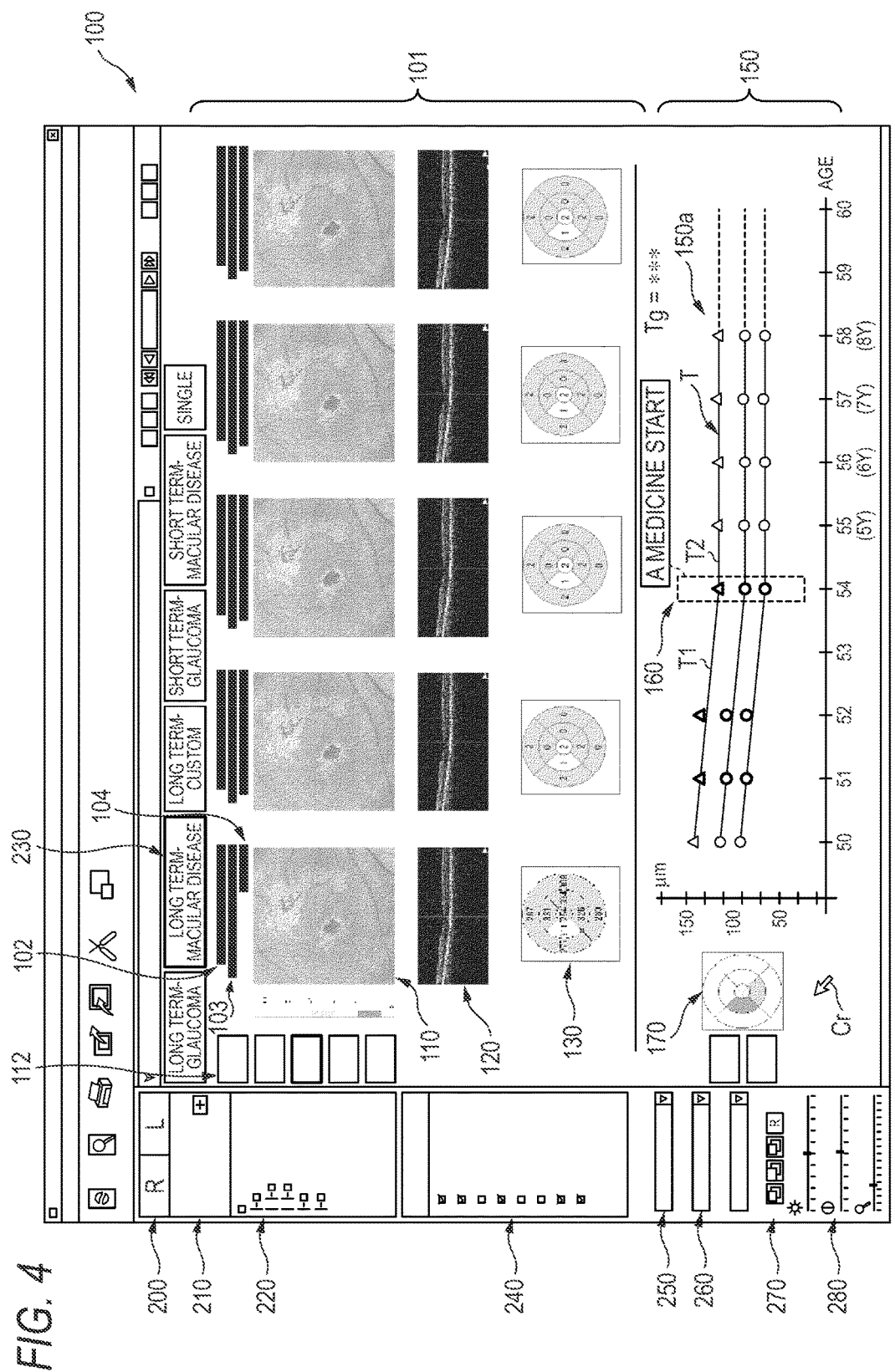
FIG. 4 is a diagram showing a display screen showing one example of assignment of event information.

An interval of implementation of periodic examination is generally on a monthly to trimonthly basis. For example, the retina thickness information is stored every month. Temporal change information is outputted to the display unit 1 as a graph as shown in FIG. 4.

Event information (for example, a kind of treatment to the eye E or the time and date of treatment) about the eye is stored in the storage unit 30 through the input unit 4. An input of the event information includes a configuration of selection by, for example, pull-down to a kind and an examination date on the display unit 1, and a direct input using a keyboard etc. The event information is outputted to the display unit 1 as the graph as shown in FIG. 4.

Examination data by another apparatus other than the optical coherence tomography 10 is stored in the storage unit 30 through the input unit 4. Examination information obtained by another apparatus includes, for example, an eyesight examination result, a visual field examination result or a photography image in a fundus camera. An input of the examination data by another apparatus includes a configuration of selection by, for example, pull-down to a kind and an examination date on the display unit 1, and a direct input using a keyboard etc.

The optical coherence tomography (OCT) 10 is connected to the fundus analysis apparatus in a state capable of communication of a signal, and various data (for example, tomography image data, front image data, various photography conditions (for example, an examination date or a scan position of measurement light) at the time of acquiring an image, etc.) acquired by the optical coherence tomography (OCT) 10 is stored in the storage unit 30.

FIG. 4 is a diagram showing a screen for displaying acquired measurement data on one screen and observing a temporal change in measurement data of the eye by a list.

At least a display region 100 for follow-up observation is formed on a list screen. The display region 100 for follow-up observation includes an analysis result display region 101 for displaying analysis results acquired at different dates using the optical coherence tomography 10 in time sequence, and a graph display region 150 for displaying a time-series graph.

In the analysis result display region 101, for example, analysis results are arranged from left to right in time sequence, and examination date information 102, image evaluation information 103, baseline information 104, a retina thickness map 110, a tomography image 120 and an analysis chart 130 are displayed.

An examination date and an age of a subject at the examination date are displayed in the examination date information 102. As the image evaluation information 103, a first evaluation value (for example, SSI) for evaluating image quality of a tomography image serving as a basis for calculation of measurement data, a second evaluation value for evaluating image quality of a fundus front image acquired simultaneously with the tomography image, etc. are displayed. The baseline information 104 is, for example, information indicating a time relation of analysis results outputted on the display unit 1. In the analysis results outputted on the display unit 1, the oldest measurement data is set as a baseline as the starting date of follow-up observation. In other measurement data, elapsed time (for example, units of year and month) using the baseline as the starting date is calculated and is outputted on the display unit 1. In the present embodiment, other measurement data other than the analysis results set as the baseline is arranged in order near to the examination date of the baseline.

The retina thickness map 110 is a color map indicating two-dimensional distribution of retina thickness of the eye, and is color-coded according to layer thickness. The retina thickness map 110 includes a thickness map indicating a thickness of a retina layer, a comparison map indicating a result of comparison between a thickness of a retina layer of the eye and a thickness of a retina layer of the normal eye stored in the normal eye database, a deviation map indicating a deviation of a thickness of a retina layer of the eye from a thickness of a retina layer of the normal eye stored in the normal eye database by a standard deviation, an examination date comparison thickness difference map indicating a difference between each examination date and a thickness, etc. Instead of the maps displayed in a display region of the retina thickness map 110, a fundus front image acquired by a scanning laser ophthalmoscope (SLO), a fundus camera, etc. may be displayed.

Figure 5:
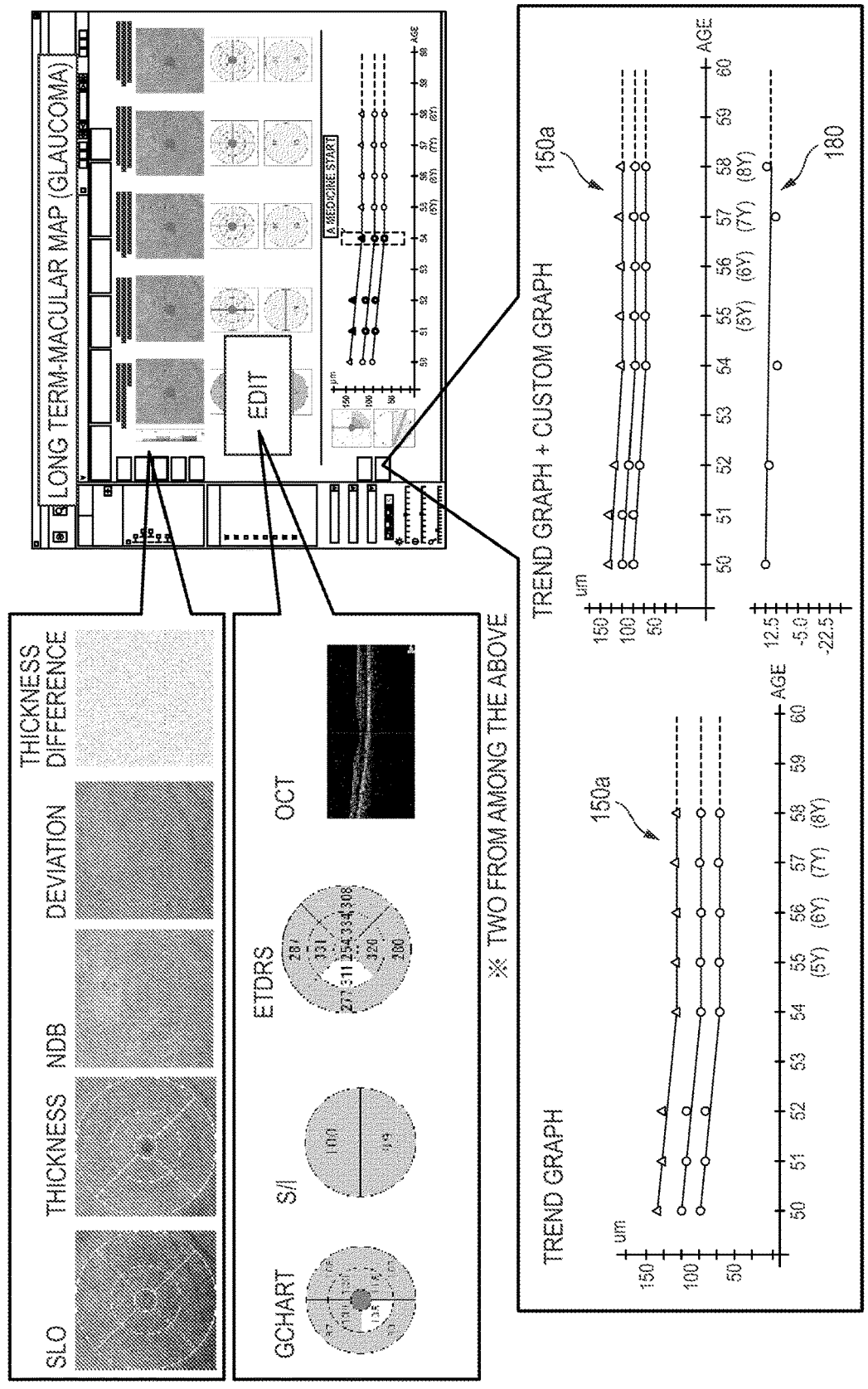
FIG. 5 is a diagram showing one example of customization of data displayed on the display screen of FIG. 4.

A two-dimensional image displayed in the display region of the retina thickness map 110 can be selected by a two-dimensional image selective region 112. In the two-dimensional image selective region 112, for example, a kind of two-dimensional image outputted to the display unit 1 is displayed discriminably. FIG. 4 is in a state in which the comparison map is selected. An examiner can output a desired two-dimensional image by selecting a desired map or a fundus front image in a customization screen as shown in FIG. 5 (see FIG. 5).

In a tomography image displayed in a region in which the tomography image 120 is displayed, a tomography image corresponding to a measurement area of the retina thickness map 110 is displayed. For example, a tomography image corresponding to a line corresponding to the center of the retina thickness map 110 is displayed by default. An outputted tomography image can be selected freely, and a tomography image corresponding to a cut line freely set on the retina thickness map 110 is configured to be outputted on the display unit 1.

The analysis chart 130 is a chart for obtaining the average of two-dimensional distribution of retina thickness of the eye every region. When the retina thickness map 110 is a macular map, GCHART, an S/I chart, an ETDRS chart, etc. are displayed selectively.

Also, a numerical display region in which a layer thickness in a predetermined region is displayed by a numerical value may be assigned to the analysis chart 130. In the numerical display region, for example, an overall average retina thickness, a retina thickness in a fovea centralis, an average retina thickness (for example, 1, 2, 3 mm) within a predetermined area centered on the fovea centralis, etc. are displayed.

In the tomography image 120 and the analysis chart 130, data outputted on the display unit 1 can be selected freely, and when the retina thickness map 110 is a macular map, for example, an examiner can select two from among GCHART, an S/I chart, ETDRS and the tomography image 120. That is, the data outputted on the display unit 1 can be customized.

When the retina thickness map 110 is a papillary map, an overall chart, a two-piece chart (2 division), a TSNIT chart (4 division), a ClockHour chart (12 division), etc. are displayed selectively as the analysis chart. And, for example, an examiner can select two from among each of these charts and the tomography image 120, and the selected chart or the tomography image is outputted on the display unit 1.

<Trend Graph Display>

The CPU 20 displays a time-series graph 150a in the graph display region 150 using layer thickness data at each examination date. The time-series graph 150a has characteristics as, for example, a time-series data graph (for example, a broken line graph or a plot graph) in which the layer thickness data at each examination date is arranged in time sequence, and a trend graph indicating a trend (trend) of a temporal change in the layer thickness data at each examination date. Of course, the graph may be either the time-series data graph or the trend graph.

The time-series graph 150a is, for example, a graph in which the axis of abscissa is the time axis and the axis of ordinate is a retina thickness, and indicates a temporal change in retina thickness in the same fundus position of the same eye every examination date. Of course, a relation between the axis of abscissa and the axis of ordinate may be opposite.

The time axis formed as the axis of abscissa is expressed by, for example, an age (age) of a subject or an elapsed period (~Y) from the starting date of follow-up observation as the baseline as shown in FIG. 4.

The axis of ordinate includes a thickness value (for example, by μm), a volume value (for example, by mm3), etc. as a numerical value indicating a layer thickness of a retina layer. The layer thickness data outputted as the axis of ordinate of the trend graph includes, for example, a layer thickness value on a specific line in a tomography image, a representative value of a layer thickness value on a specific area in a tomography image, or a layer thickness value (also called analytical value data) in a specific section in an analysis chart.

The CPU 20 displays a point corresponding to layer thickness data at each examination date as a graph. In the case of creating the trend graph, the CPU 20 analyzes a trend of the layer thickness data at each examination date and displays a time-series regression line T by the layer thickness data at each examination date. The regression line T indicates a trend of a time-series change in the layer thickness data. Also, the CPU 20 displays a slope Tg of the regression line T.

For example, the CPU 20 obtains a regression line of a series of layer thickness data and also obtains a slope of the regression line. The regression line and the slope are obtained by a formula for calculating the regression line, for example, a method of least squares. An example of obtaining the regression line is shown.

Regression means that x and y can be expressed by any relational formula. In linear regression, a formula of y=ax+b is derived from n points applied to a plane, and this line is called a regression line.

In order to derive coefficients a, b, the coefficients could be substituted into the following formula. In the present example, elapsed time using an examination date of a baseline as 0 is substituted as a value of x. Also, layer thickness data (for example, analytical value data obtained by an analysis chart, retina thickness data in a certain position, or a representative value of retina thickness data in a certain region) is substituted as a value of y.

[Mathematical Formula 1]

$$a = \frac{S_{xy}}{S_{xx}}$$

$$= \frac{\sum(x_i - \bar{x})(x_i - \bar{y})}{\sum(x - \bar{x})^2}$$

$$= \frac{\sum x_i y_i - (\sum x_i \cdot \sum y_i)/n}{\sum x_i^2 - (\sum x_i)^2/n}$$

$$b = \bar{y} - a\bar{x} = \frac{1}{n}\left(\sum y_i - b\sum x_i\right)$$

The line y=ax+b obtained by the above is a regression line, a indicates a slope of the regression line.

In addition to the slope etc., a p value used in statistics may be shown on a graph. The p value is a scale indicating the possibility that a between-group difference accidentally occurs during a certain experiment. For example, the p value of 0.01 means that this result accidentally occurs one in every 100 times. As the p value is smaller, the possibility that the between-group difference occurs due to treatment is higher. Generally, for p<0.05, its data (line) is probably significant.

<Slope Information about Trend Graph and Slope Comparison Based on Normal Eye Data>

The CPU 20 may display a trend graph of the eye and a trend graph created using normal eye data on the same graph. The trend graph based on the normal eye data is acquired by calculating a regression line based on a temporal change in age layer thickness data in a normal eye without retinal disease by, for example, clinical trials.

Accordingly, an examiner can grasp a difference between the eye and the normal eye in a temporal change in retina thickness. Consequently, normality and abnormality of the eye can be checked from the temporal change to further help in the prediction of future diseases.

Also, the CPU 20 may compare temporal slope information about a regression line in the trend graph with temporal slope information about a regression line created using the normal eye data, and display a comparison result on the graph. The slope information is represented by, for example, a numerical value or an indicator.

<Trend Graph and Additional Information>

The CPU 20 displays event information 160 in the time-series graph 150a as additional information. The event information 160 is displayed in correspondence with an event occurrence date. In the case of setting the event information 160, for example, an event name (for example, "start of administration of A drug") is registered together with the occurrence date by an operation input through the input unit 4. Accordingly, an examiner can understand "when and what has been done" at a glance on the time-series graph 150a.

The event information 160 is not limited to one, and plural pieces of event information 160 can be inputted. An elapsed period from the event occurrence date may be added to the axis of abscissa of the time-series graph 150a. Accordingly, the elapsed time from the event occurrence date is associated with a temporal change in layer thickness data.

The CPU 20 may separately conduct trend analyses before and after the event occurrence date in the event information 160. Accordingly, the examiner can easily grasp a change in retina thickness by the event.

The CPU 20 analyzes a trend of layer thickness data at each examination date before the event occurrence date using the event occurrence date of the event information 160 as a boundary, and displays a time-series regression line T1. Accordingly, the examiner can easily grasp the trend of layer thickness data before the event occurrence.

The CPU 20 analyzes a trend of layer thickness data at each examination date after the event occurrence date using the event occurrence date of the event information 160 as the boundary, and displays a time-series regression line T2. Accordingly, the examiner can easily grasp the trend of layer thickness data after the event occurrence.

Addition of the event information 160 can be set in plural places. A new trend analysis is conducted every time an event is added. When two events are added, for example, a first regression line by layer thickness data before a first event, a second regression line by layer thickness data between the first event and a second event, and a third regression line by layer thickness data after the second event are obtained, and the regression lines are outputted on the display unit 1.

<Analytical Region Display about Trend Graph>

The CPU 20 may display analytical region display 170 showing an analytical region corresponding to layer thickness data shown by the time-series graph 150a together with the time-series graph 150a. Information displayed in the analytical region display 170 is represented by any of, for example, a diagram, a table and an image. Accordingly, an examiner can easily check a position of the displayed graph.

Description will hereinafter be made by taking the case of a trend graph by layer thickness data obtained by an analysis chart as an example. The CPU 20 displays a chart in which a section corresponding to the analysis chart is formed as shown in FIG. 4 as the analytical region display 170. For example, a color of a section set on the chart as a trend graph creation region is associated with at least any of a regression line and a point of a graph corresponding to layer thickness data in its section. For example, a regression line and a point of layer thickness data corresponding to a section of a pink color are represented by the pink color on the time-series graph 150a. From a relation between the analytical region display 170 and the time-series graph 150a, the examiner can easily grasp a measurement position corresponding to layer thickness data shown by the time-series graph 150a.

Graphs by plural layer thickness data with mutually different sections on the time-series graph 150a may be displayed simultaneously. The CPU 20 may indicate a measurement position corresponding to each of the graphs in the analytical region display 170. For example, a section corresponding to each of the graphs is colored in a chart in the analytical region display 170.

The CPU 20 shares a selective region for selecting a section displayed on the time-series graph 150a as the analytical region display 170. For example, when a section in the analytical region display 170 is specified using a cursor Cr displayed on the display unit 1 and the portion to be displayed as a graph is selected and inputted (for example, clicked), the graph of the selected section is displayed. When a specific section in an analysis chart displayed in an analysis result display region 100 is selected, the CPU 20 may display a graph of the selected section.

<Custom Graph>

The CPU 20 may display a custom graph 180 in addition to the time-series graph 150a described above. The custom graph 180 graphically forms examination data after an examination date by another apparatus different from the optical coherence tomography (see FIG. 5).

For example, a format in which the time-series graph 150a and the custom graph 180 as shown in FIG. 5 are arranged and displayed is obtained. The custom graph 180 graphically displays a temporal change in examination data by another apparatus which wants to compare and display examination data together with a temporal change in layer thickness data in the time-series graph 150a.

Examples displayed as the custom graph include values such as an MD value used in a perimeter etc. or an eyesight value measured by an eyesight examination device.

FIG. 5 shows a state in which the time-series graph 150a and the custom graph 180 are longitudinally arranged, but it is not limited to this state, and a display layout in which the time-series graph 150a and the custom graph 180 are superimposed and displayed on one graph may be used.

<Auxiliary Screen>

A left-right eye switching button 200, an eye axial length/eye refractive power display region 210, a scan pattern setting region 220, a disease and period selective region (hereinafter a selective region) 230, an examination date selective region 240, a display format selective region 250, an analysis layer selective region 260 and a display screen adjusting unit 270 are formed as an auxiliary screen.

The switching button 200 is a button for selecting an eye for outputting an analysis result between left and right eyes. The CPU 20 outputs a graph and the analysis result corresponding to the eye selected by the switching button 200 to an analysis result display region.

For example, an eye axial length value, an eye refractive value of the eye, etc. are displayed in the eye axial length/eye refractive power display region 210 of the eye.

The scan pattern setting region 220 is a display region for setting a scan pattern outputted to the analysis result display region.

Figure 6:
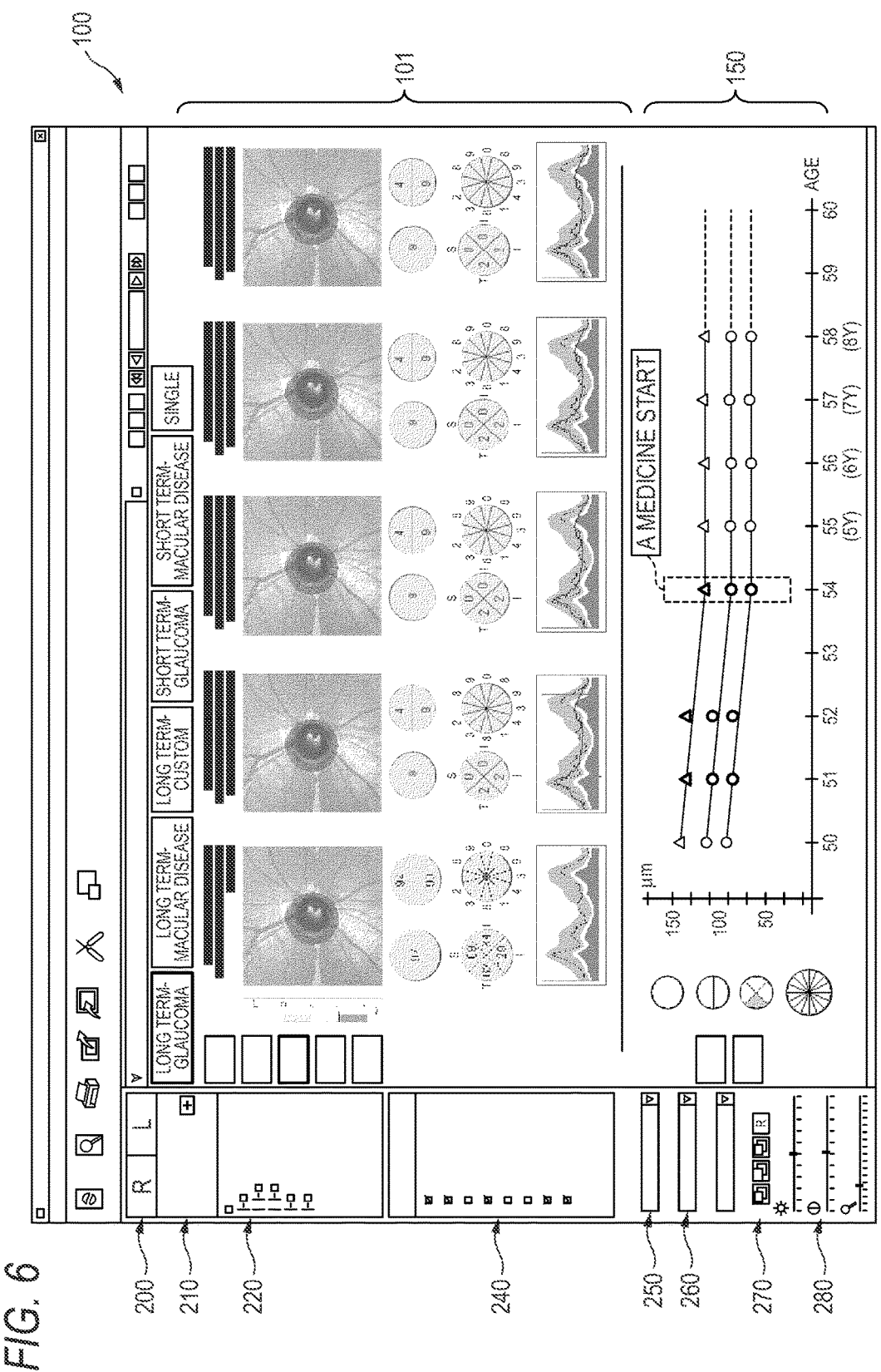
FIG. 6 is a diagram showing one example of an analysis result display screen according to papilla analysis.
Figure 7:
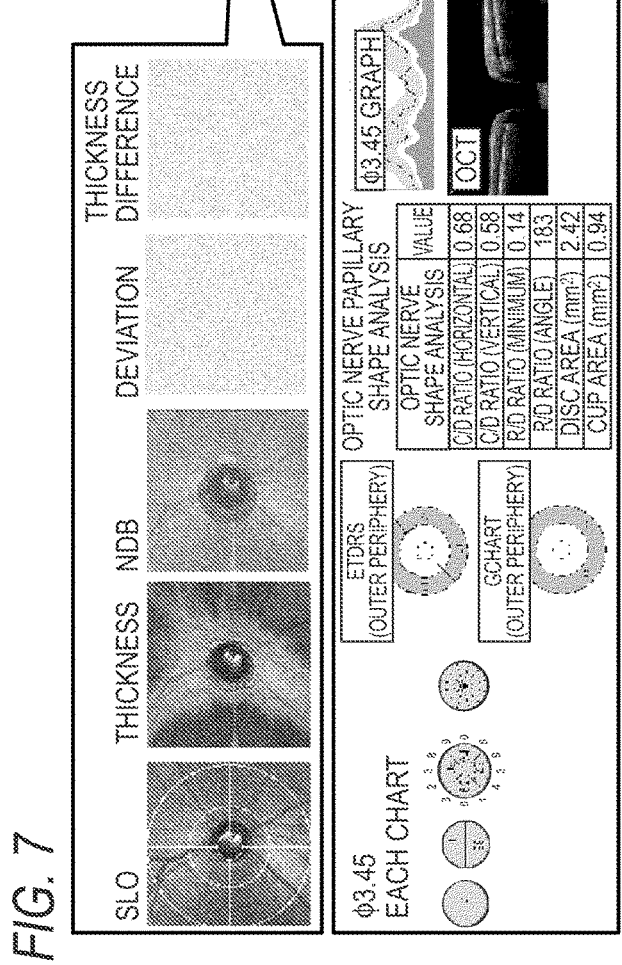
FIG. 7 is a diagram showing one example of customization on the analysis result display screen according to papilla analysis.
Figure 7:
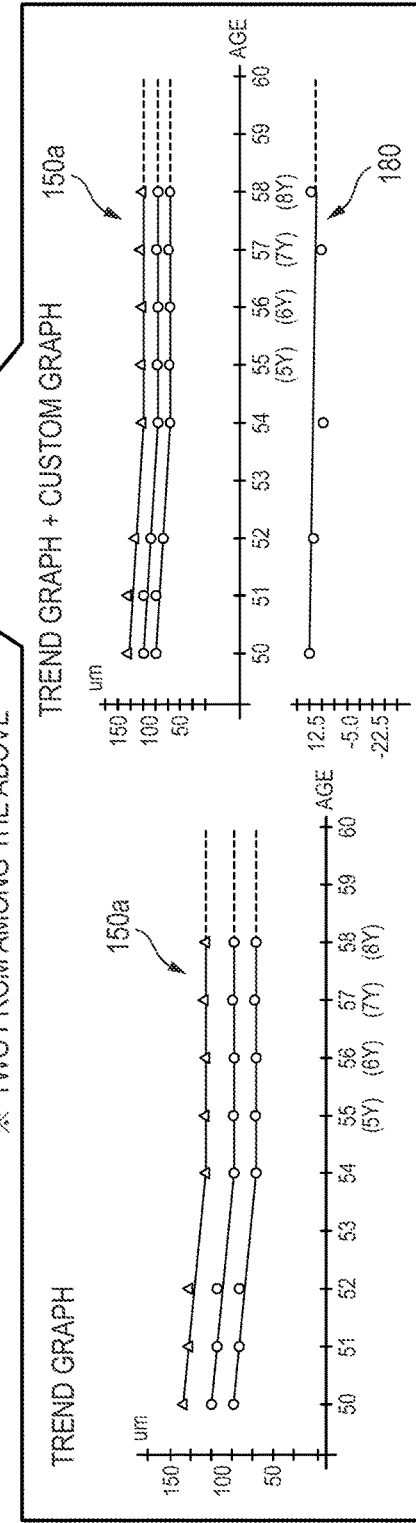

A scan pattern acquired by the optical coherence tomography from the start of examination to the present, and a tree including an item indicating a region on a fundus acquired by the scan pattern are displayed in the scan pattern setting region 220. The item of the tree of the setting region 220 is classified by combination of the scan pattern and a photography region on the fundus. For example, a macular map indicates OCT data obtained at the time of executing a raster scan centered on a macular region on the fundus. A papillary map indicates OCT data obtained at the time of executing a raster scan centered on a papillary region on the fundus. Also, a papillary radial indicates OCT data obtained at the time of executing a radial scan centered on a papillary region of the fundus. FIG. 6 is a diagram showing one example of the display region 100 for follow-up observation in the case of selecting the papillary region as the photography region, and FIG. 7 is a customization screen in the case of selecting the papillary region as the photography region.

Consequently, an examiner selects a desired item from among items selected by a tree format in the setting region 220 (for example, operation of a click on the item). The CPU 20 outputs the selected corresponding analysis result to the display unit 1.

In the selective region 230, a result outputted to the analysis result display region is distinguished by a disease and a follow-up observation period, and the disease and the period can be selected.

For example, plural tabs are displayed in the selective region 230 and, more concretely, items are classified by combinations of long term-glaucoma, long term-macular disease, long term-custom, short term-glaucoma, short term-macular disease, retina disease including custom display, long term-short term, singly. When the examiner selects a desired item, a tree corresponding to the selected item is displayed on the scan pattern setting region.

The item about a long term such as long term-glaucoma, long term-macular disease, or long term-custom is an item for making long-term follow-up observations. When this item is selected, analysis results acquired at different dates are simultaneously displayed in the analysis result display region and also, a trend graph created based on these analysis results is displayed on the display unit 1.

The item about a short term such as short term-glaucoma or short term-macular disease is an item for making short-term follow-up observations. When this item is selected, two analysis results acquired at different dates are simultaneously displayed in the analysis result display region. A retina thickness map, an analysis chart, a tomography image, etc. in the two analysis results are displayed relatively larger than the case of selecting the long-term item.

The item about custom is an item for displaying at least two display items selected by the examiner from among plural display items (for example, each retina thickness map, each analysis chart or an OCT image) for plural analysis results acquired at different dates. The display item displayed in the item about custom is previously selected through operation in the input unit 4 by the examiner.

The examination date selective region 240 is a selective region for selecting an examination date outputted to the display region 100.

In the examination date selective region 240, acquisition dates (examination dates) acquired from the past to the present for the item selected in the setting region 220 are displayed as a list.

A checkbox is respectively formed in each examination date, and when an examination date to be outputted to an analysis result region is checked, an analysis result corresponding to the checked examination date is outputted to the analysis result display region 100. Also, when the checkbox is unchecked, analysis result display corresponding to the unchecked examination date is cleared from the analysis result display region 100.

The CPU 20 may create the time-series graph 150a based on the analysis result corresponding to the checked examination date and display the created time-series graph 150a on the display unit 1. As described above, the analysis result serving as a basis for the time-series graph 150a can be selected every examination date to thereby create a trend graph based on a proper analysis result. For example, even when image quality of an OCT image obtained at a certain examination date is low (for example, at the time of occurrence of the blink), the corresponding examination date is not selected to thereby be excluded as basic data of the trend graph.

<Auxiliary Item Detailed Description>

The display format selective region 250, the analysis layer selective region 260 and the display screen adjusting unit 270 are formed in an auxiliary item display region. The display format selective region 250 is a region for selecting a display format of an analysis chart and, for example, either a thickness display mode or a difference display mode is selected. In the case of selecting the thickness display mode, the CPU 20 displays an analysis chart for representing a retina thickness value as it is for each analysis result at different examination dates. In the difference display mode, the CPU 20 displays an analysis chart for representing a retina thickness value as it is for an analysis result set in a baseline, and displays an analysis chart for representing a retina thickness value as a difference in the analysis result set in the baseline for other analysis results other than the baseline.

The analysis layer selective region 260 is a display region for setting the start and the end of an analysis layer outputted as a retina thickness map and an analysis chart. When the analysis layer is set by the analysis layer selective region 260, the CPU 20 acquires layer thickness information about the set analysis layer, and creates the retina thickness map and the analysis chart based on the acquired layer thickness information. The created retina thickness map and the analysis chart are outputted to the display unit 1.

The display screen adjusting unit 270 is a display region for adjusting, for example, a display color of an analysis result or a contrast of the display unit 1.

In the case of taking follow-up photography based on a photographic pattern (BaseLine) of a preset criterion, the CPU 20 may correct a positional deviation between tomography images by image processing. Accordingly, any position set in BaseLine is automatically reflected on FollowUp data. Consequently, it becomes unnecessary to set any position individually.

The embodiment described above can be represented as described below.

(1) The controller displays a time-series graph created from plural OCT data acquired at different dates together with additional information.

(2) The time-series graph obtained from plural data indicates a trend analysis graph.

(3) The controller appends event information about surgery, medication, etc. together with the date and time on the graph of (1).

(4) A trend analysis is newly conducted from a position of the event set in (3), and a trend graph before the event and a trend graph after the event are displayed. Also, elapsed time from the event position is displayed.

(5) A slope of the trend analysis graph obtained from plural data in (2) is compared with a slope of a graph by normal eye data, and a comparison result is displayed.

(6) The data used in the graph in (1) or (2) is displayed in a diagram and a table together with the graph so as to understand which portion the data corresponds to.

(7) The diagram and the table displayed together with the graph in (6) are a chart or a table in a map etc., and the portion displayed in the graph is distinguished and displayed so as to be understood by a color. Also, graph display is switched in the case of clicking the portion to be displayed in the graph in the diagram and the table.

(8) Another time-series graph created from data inputted by a user is together displayed separately from the time-series graph created from plural data acquired at different dates in (1) or (2).

(9) The data inputted by the user in (8) is at least any of an MD value and eyesight.

<Output of Two-Dimensional Image at Each Examination Date for Specific Period on Time-Series Graph>

Figure 8:
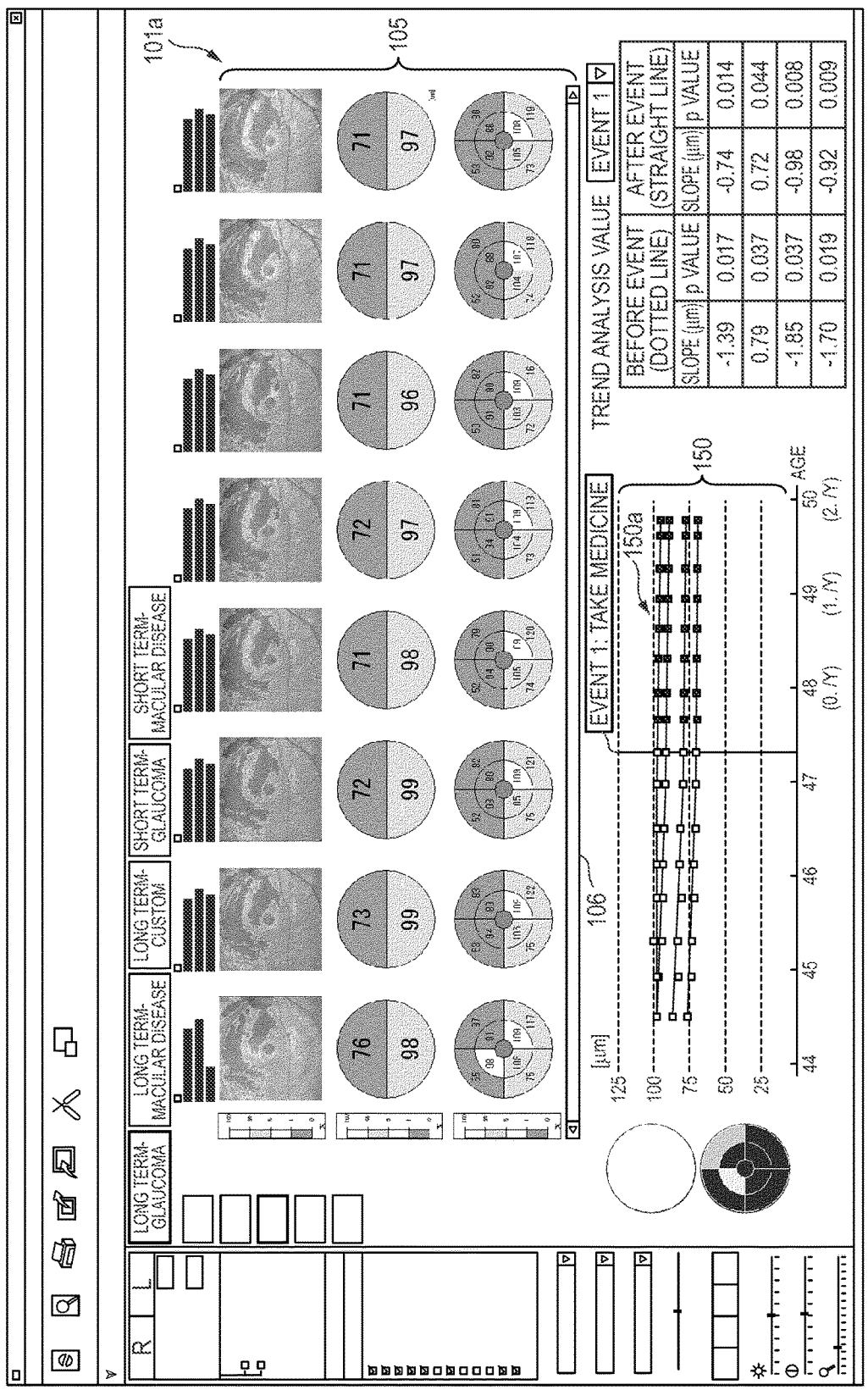
FIG. 8 is a diagram of a display screen showing one example in the case of outputting a two-dimensional image at each examination date for a specific period.

FIG. 8 is a diagram showing one example in the case of outputting a two-dimensional image for a specific period on a time-series graph. The CPU 20 displays the time-series graph 150*a* on a display screen and also, arranges and displays the two-dimensional image (for example, a photography image or an analysis image) for a period for which analysis results are outputted on the time-series graph 150*a*.

Here, in the case of outputting two-dimensional images for all the period for which analysis results are outputted when the period for which analysis results are collected is a long period, or when the number of collections of analysis results is large, each of the two-dimensional images is scaled down and it is difficult for an examiner to check the analysis results.

Hence, the CPU 20 may output each two-dimensional image 105 for a specific period in time sequence. The two-dimensional image 105 is a two-dimensional image at each examination date for the specific period within the period for which analysis results are outputted on the time-series graph 150*a*. A two-dimensional image display region (hereinafter a display region) 101*a* is used as a display region for arranging and displaying plural two-dimensional images 105 for the specific period.

For example, the CPU 20 may set the two-dimensional image 105 outputted to the display region 101*a* based on an operation signal from the input unit 4 to the display region 101*a*. Concretely, the CPU 20 may store image data for arranging the two-dimensional images for the period for which analysis results are outputted on the time-series graph 150*a* in memory 40, and output a specific part of the image data stored in the memory 40 according to the operation signal from the input unit 4 to the display region 101*a* as the two-dimensional image 105 for the specific period. Of course, the CPU 20 may create the two-dimensional images outputted to the display region 101*a* sequentially according to the operation signal from the input unit 4. In this manner, the two-dimensional image 105 outputted to the display region 101*a* is set or changed through the operation from the input unit 4.

As operation to the display region 101*a*, for example, the CPU 20 may set or change the two-dimensional image 105 outputted to the display region 101*a* by scroll operation, drag operation, slide operation, flick operation, etc. in the display region 101*a*.

The operation to the display region 101*a* also includes operation to a display region for operation displayed in the vicinity of the two-dimensional image 105 arranged in time sequence. For example, when an operation signal for scrolling a scroll bar 106 formed between the two-dimensional image 105 and the time-series graph 150*a* is inputted from the input unit 4, the CPU 20 may set or change the two-dimensional image 105 outputted to the display region 101*a* according to movement of the scroll bar 106 on the display screen.

When the two-dimensional image 105 outputted to the display region 101*a* is selected, the CPU 20 may discriminably display the specific period for which the two-dimensional image 105 is outputted on the time-series graph 150*a*.

For example, the CPU 20 may output plots or lines (for example, a broken line or a trend line) on the time-series graph 150*a* for the specific period and other periods in different display modes (for example, different colors, different line types, the presence or absence of filling, etc.) (see FIG. 8).

Accordingly, an examiner can observe the two-dimensional image 105 for a desired specific period and also, check the period for which the two-dimensional image 105 is outputted on the time-series graph 150*a*.

The CPU 20 may set or change the two-dimensional image 105 outputted to the display region 101*a* based on the operation signal from the input unit 4 to the display region 150.

For example, the CPU 20 may display two-dimensional images in time sequence for a specific period corresponding to an operation position on the display region 150. For example, in the case of clicking on a display region in which the time-series graph is displayed, the CPU 20 displays two-dimensional images in time sequence using the clicked display position as a starting point of the period.

Also, a position of a line for dividing a specific period and another period on the time-series graph 150*a* may be adjusted to display a two-dimensional image for the period specified by the adjusted line in time sequence in the display region 101a as the two-dimensional image 105.

Operation to the display region 101a also includes operation to a display region for operation displayed in the vicinity of the time-series graph 150a. For example, when an operation signal for scrolling a scroll bar formed under or over the time-series graph 150a is inputted from the input unit 4, the CPU 20 may set or change the two-dimensional image 105 outputted to the display region 101a according to movement of the scroll bar.

When the two-dimensional image 105 for the specific period is outputted to the display region 101a, a technique for large displaying the two-dimensional image 105 for the specific period and relatively small displaying two-dimensional images for other periods is also included.

<Fixed Display of Part of Two-Dimensional Image>

FIG. 9 is a diagram showing one example in the case of fixing and displaying a part of a two-dimensional image.

Figure 9A:
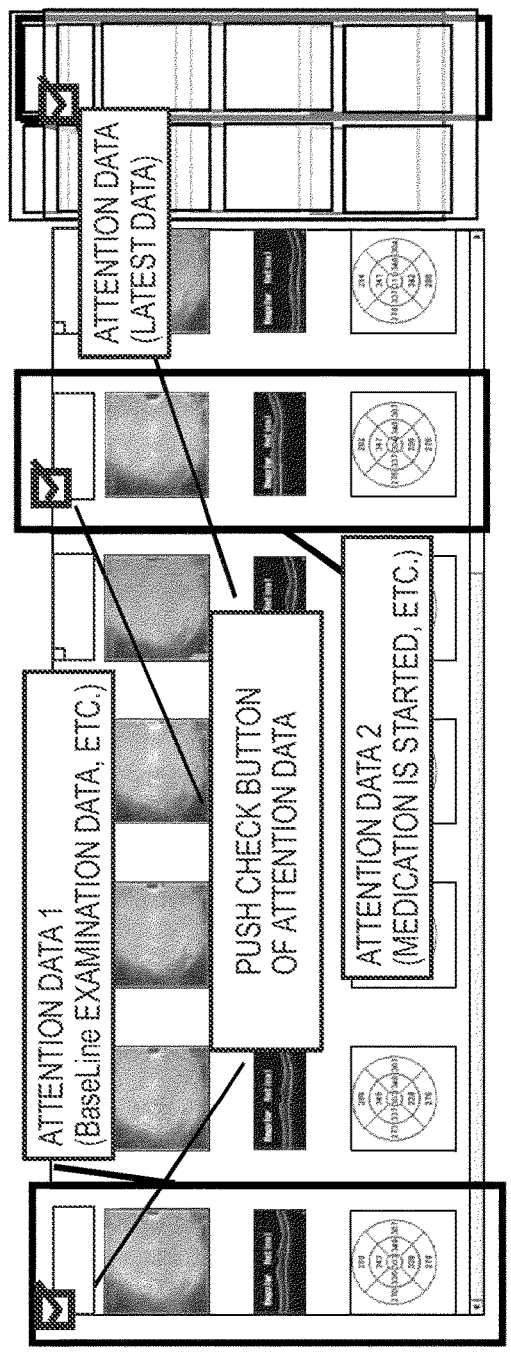
FIG. 9A is a diagram showing one example of a display screen in the case of fixing a part of a two-dimensional image.

For example, when a checkbox assigned to each of the two-dimensional images 105 is pushed, the CPU 20 sets these images as a fixed display image (see FIG. 9A). Of course, one two-dimensional image 105 or plural two-dimensional images 105 may be selected.

Figure 9B:
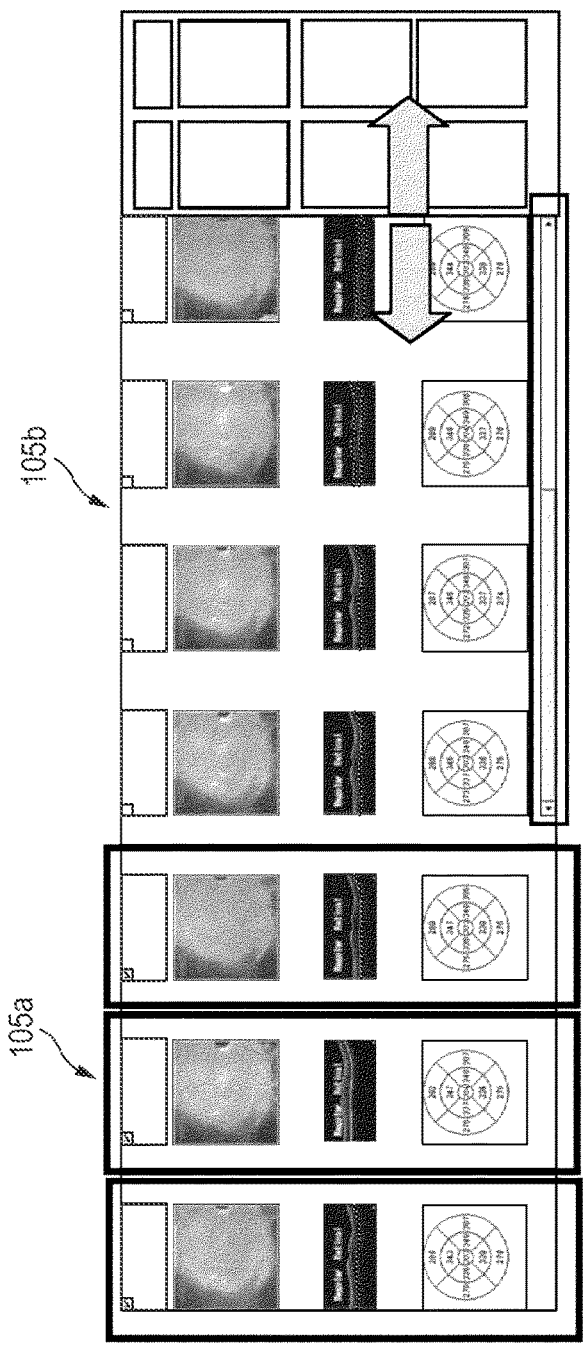
FIG. 9B is a diagram showing one example of the display screen in the case of changing other two-dimensional images with respect to fixed display.

Then, the CPU 20 displays two-dimensional images 105a set as the fixed display images mutually adjacently in the display region 101a (see FIG. 9B). Also, the CPU 20 displays other two-dimensional images 105b in time sequence in a display region different from the display region 101a of the fixed display images Here, when instructions to change the two-dimensional images 105b are received through operation of the input unit 4 (for example, scroll operation, drag operation, slide operation, flick operation, etc. in the two-dimensional images 105b), the CPU 20 changes other two-dimensional images 105b outputted to the display region 101a.

In the description of the example described above, the fixed display image is selected on the two-dimensional image 105, but it is not limited to this. For example, the fixed display image may be selected on the time-series graph 150a. For example, when a plot on the time-series graph 150a is clicked, the two-dimensional image of an examination date corresponding to the plotted analysis results is selected as the fixed display image.

Figure 10:
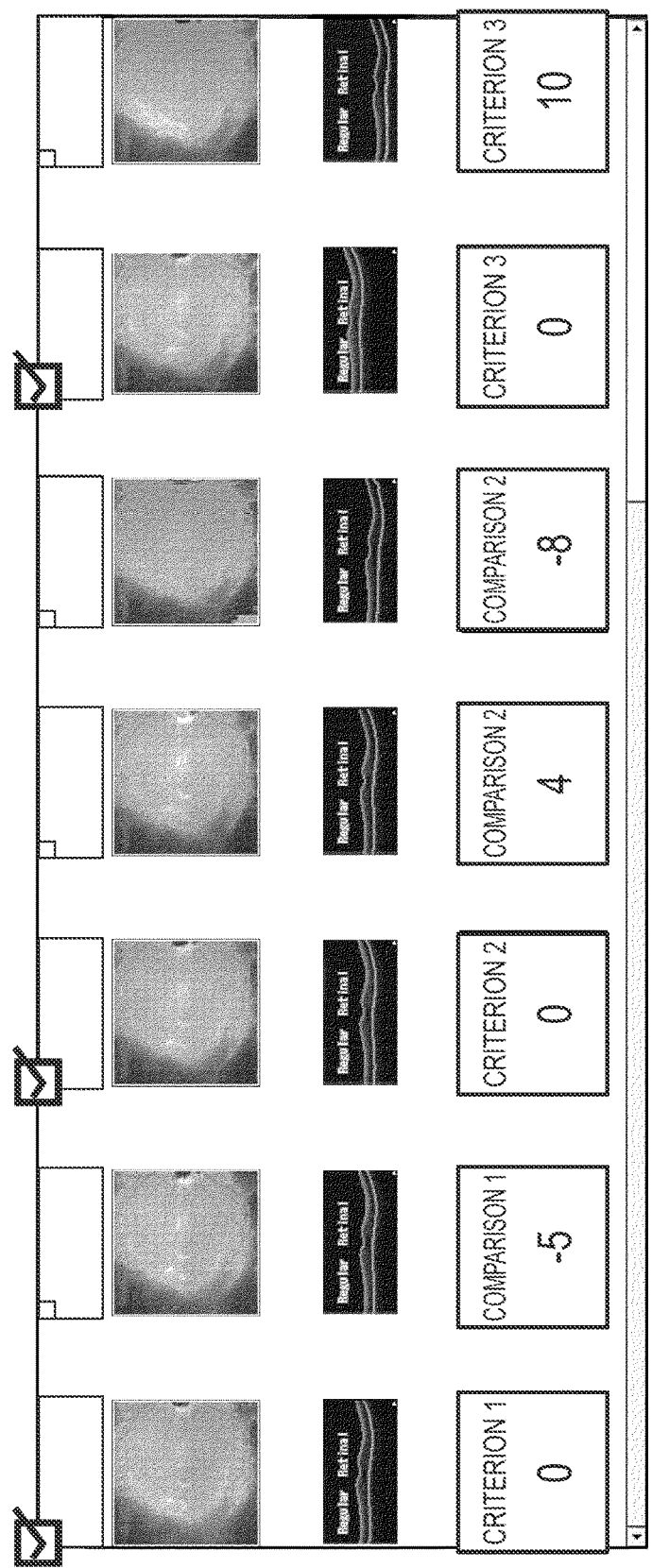
FIG. 10 is a diagram showing one example in the case of making a retina thickness comparison from attention examination data.

The CPU 20 may display a two-dimensional image indicating a result of comparison between an analytical value corresponding to the fixed and displayed two-dimensional images 105a and an analytical value corresponding to other two-dimensional images 105b (see FIG. 10). FIG. 10 is a diagram showing one example of a retina thickness comparison from attention examination data. Examination data of criterion 1 is compared with an analytical value of comparison 1, and examination data of criterion 2 is compared with an analytical value of comparison 2, and examination data of criterion 3 is compared with an analytical value of comparison 3, and comparison results are displayed.

<Setting of Follow-Up Observation Position on Tomography Image>

In follow-up outputs of analysis results acquired at different examination dates, the CPU 20 may, for example, function as image analysis means for analyzing a fundus tomography image stored in the storage unit 30 and obtaining an analysis result (for example, a retina thickness) and extracting the analysis result of at least a part of the tomography image selected through selection instructions from an examiner. It is useful to obtain the retina thickness as the analysis result in the case of diagnosing a lesion of a fundus, but the analysis result is not limited to the retina thickness as described in <Outline>.

Figure 11:
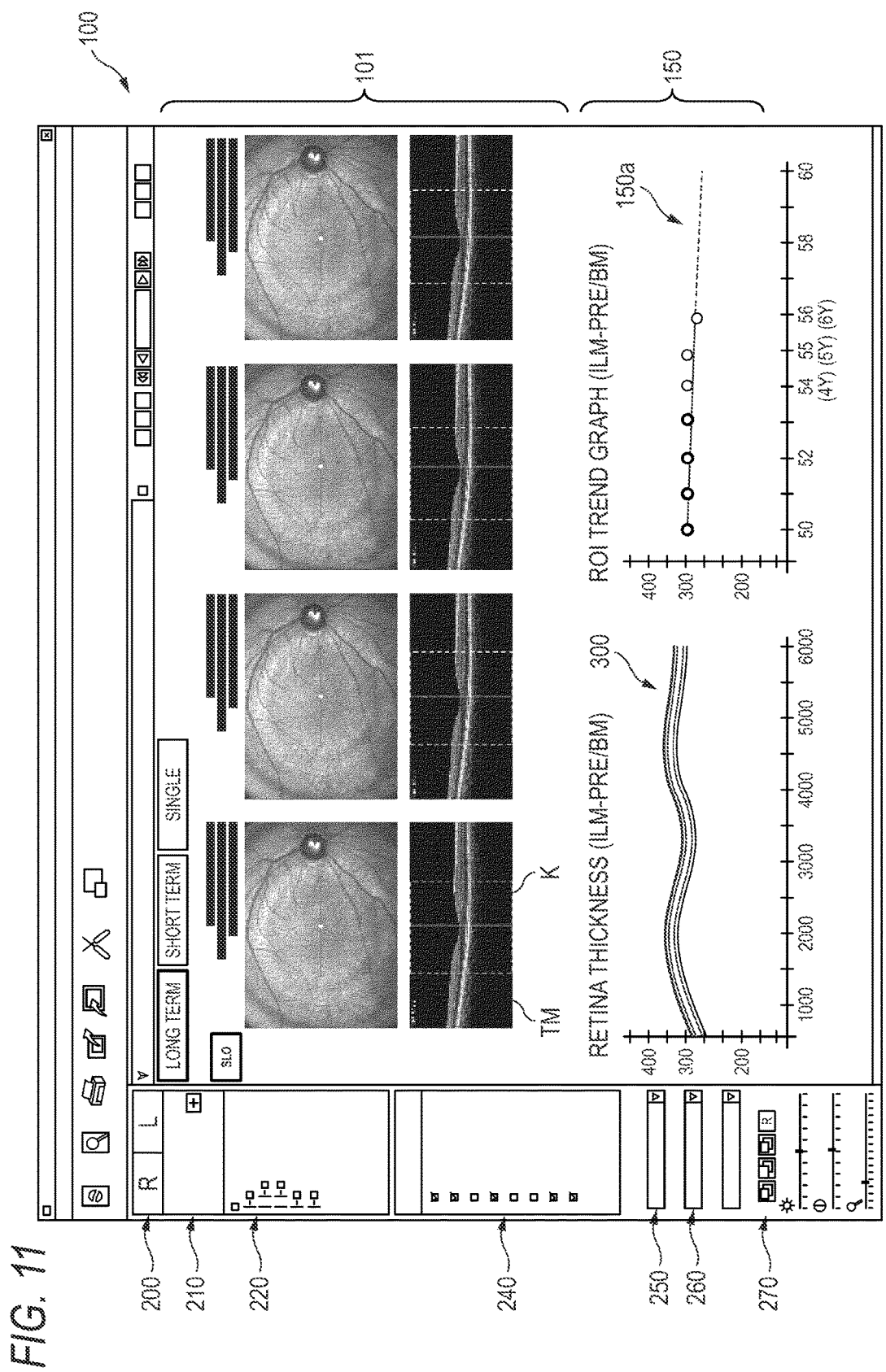
FIG. 11 is a diagram showing one example of a display screen of setting a follow-up observation position on a tomography image.

One example is shown below. The following example shows an example using a tomography image obtained by line scanning of a macular region on a fundus of the eye by the optical coherence tomography 10. An OCT image shown in FIG. 11 is a macular line image.

When a scan pattern is a one-dimensional scan, a fundus front image, a tomography image TM, a retina thickness graph 300 and the time-series graph 150a are displayed in the display region 100 for follow-up observation. The one-dimensional scan includes scan patterns of a multi-line scan (plural line scans separated mutually), a cross scan (a line scan crossed mutually (for example, a cross-shaped cross)), a circle scan, etc. in addition to the line scan.

In the retina thickness graph 300, the axis of abscissa shows a distance from a starting point and the axis of ordinate shows a thickness from a start layer to an end layer of an analysis layer. In the retina thickness graph 300, retina thickness data acquired at different examination dates is displayed on the same graph. The retina thickness graph 300 is displayed in, for example, a region next to the time-series graph 150a. When three or more examination dates are selected, three or more retina thickness data acquired at different examination dates are displayed on the same graph in the retina thickness graph 300 (see FIG. 11).

In the case of the multi-line scan, the cross scan, etc., plural tomography images are acquired. In this case, the retina thickness graph corresponding to each of the tomography images may be simultaneously displayed on the display unit 1.

<Setting of Line on Tomography Image>

Figure 12:
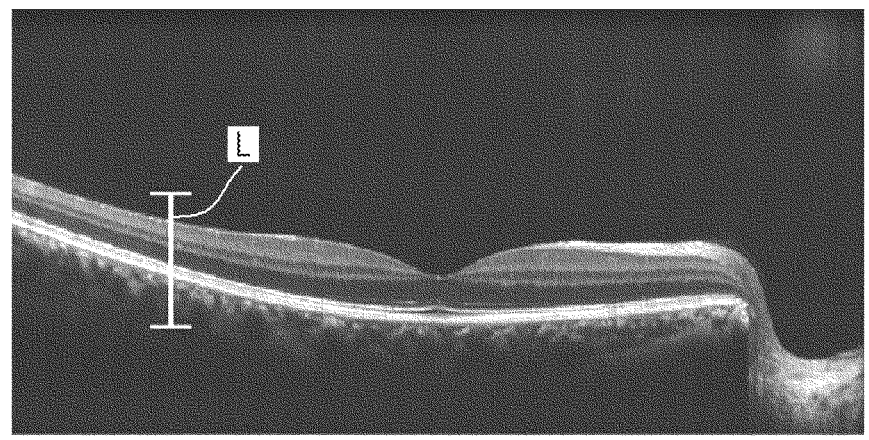
FIG. 12 is a diagram showing one example of a display screen of setting a follow-up observation position using line display on a tomography image.

FIG. 12 is an example of one-dimensionally setting a position to make follow-up observations on the tomography image TM. For example, the CPU 20 electronically displays line display L on the tomography image TM displayed in the display region 100 for follow-up observation. The line display L is displayed on the tomography image TM by predetermined operation (for example, right-click operation).

The CPU 20 receives an operation signal from the input unit 4, and moves the line display L on the tomography image TM. The line display L is used for setting a line by any two points on OCT data. The line display L is, for example, displayed in parallel with a depth direction and is used for acquiring layer thickness data in a specific position in the tomography image. Any two points on OCT data have only to be able to be set and, for example, it may be configured to specify a line by click operation of a mouse. Also, a display shape of the line display L is not limited to that of FIG. 12, and the line has only to be able to be set on the tomography image.

The CPU 20 sets a line set through the input unit 4 as a graph creation region. When a line by the line display L is set in at least one tomography image, a line is set in the same position on another tomography image, and is set as the graph creation region. That is, the CPU 20 reflects the line set on a certain tomography image with respect to another image. Accordingly, a position selected by an examiner on the tomography image is set as the graph creation region. The same position does not need to be completely the same position, and could be at the level at which the position can be regarded as the same position capable of making follow-up observations.

The CPU 20 acquires layer thickness data on the line set by the line display L in layer thickness data of the eye at each examination date. In a retina layer in which layer thickness data is outputted in the retina layer on the line, a start layer and an end layer are preset in the analysis layer selective region 260. The CPU 20 creates the time-series graph 150a including the acquired layer thickness data at each examination date, and outputs the created time-series graph 150a on the display unit 1.

Accordingly, the examiner can easily make follow-up observations of the layer thickness data corresponding to an attention position since the time-series graph 150a corresponding to the line noted by the examiner on the tomography image can be outputted.

In the case of a multi-line scan, a cross scan, etc., plural tomography images with different scan positions (a starting point and an ending point of a scan) are acquired at each examination date, and the plural tomography images are displayed on the display unit 1. When a line by the line display L is set in at least one tomography image, a line may be set in a position on another tomography image with a different scan position to be set as the graph creation region. In this case, the line may be set in a region corresponding to the same distance with respect to a starting point and the position in which the line is set by the line display L on another tomography image with the different scan position.

<Setting of Area on Tomography Image>

Figure 13:
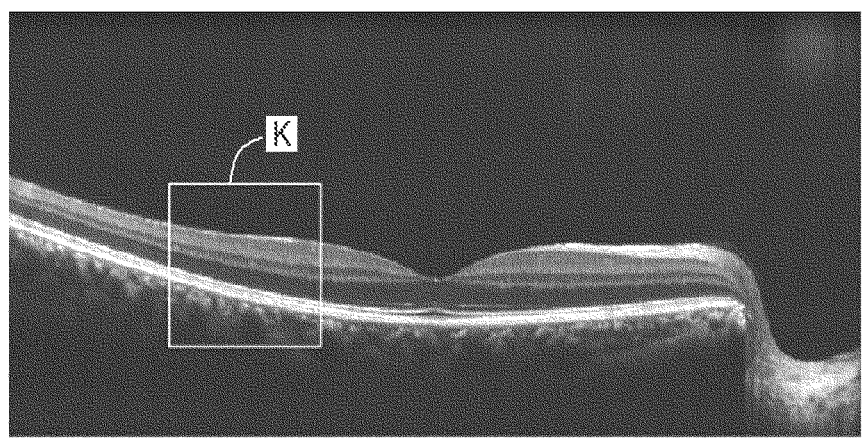
FIG. 13 is a diagram showing one example of a display screen of setting a follow-up observation position using frame display on a tomography image.

FIG. 13 is an example of two-dimensionally setting a position to make follow-up observations on a tomography image. For example, the CPU 20 electronically displays a frame K on a tomography image TM displayed in the display region 100 for follow-up observation. The frame K is displayed on the tomography image TM by predetermined operation. For example, the frame K is displayed by drag operation in an oblique direction with any one point on the tomography image TM specified.

The CPU 20 receives an operation signal from the input unit 4, and adjusts a display position and a size of the frame K on the tomography image TM. The frame K is used for setting, for example, any area (two-dimensional region) on OCT data. The frame K is, for example, displayed so as to surround at least a part of the tomography image TM and is used for acquiring layer thickness data in a specific area in the tomography image TM. Any area on OCT data has only to be able to be set and, for example, it may be configured to specify an area by click operation of a mouse or touch operation on a touch panel. Also, a display shape of the frame K is not limited to that of FIG. 13, and the area has only to be able to be set on the tomography image TM.

The CPU 20 sets an area set through the input unit 4 as a graph creation region. When an area by the frame K is set in at least one tomography image TM, an area is set in the same position on another tomography image, and is set as the graph creation region. That is, the CPU 20 reflects the area set on a certain tomography image TM with respect to another image. Accordingly, a region selected by an examiner on the tomography image acquired at each examination date is set as the graph creation region. The same position does not need to be completely the same position, and could be at the level at which the position is regarded as the same position capable of making follow-up observations.

The CPU 20 acquires plural layer thickness data included inside the area set by the frame K in layer thickness data of the eye at each examination date. In a retina layer in which layer thickness data is outputted in the retina layer inside the area, a start layer and an end layer are preset in the analysis layer selective region 260. The CPU 20 creates the time-series graph 150a including the acquired layer thickness data at each examination date, and outputs the created time-series graph 150a on the display unit 1.

The CPU 20 calculates a fundamental statistic (for example, a representative value or degree of scattering) of each layer thickness data inside the area. The CPU 20 creates the time-series graph 150a including the fundamental statistic of the acquired layer thickness data at each examination date, and outputs the created time-series graph 150a on the display unit 1.

Accordingly, the examiner can easily make follow-up observations of the layer thickness data corresponding to a position of interest since the time-series graph 150a corresponding to the area noted by the examiner on the tomography image can be outputted.

An ROI in the drawing means a Region of Interest.

In the case of a multi-line scan, a cross scan, etc., plural tomography images with different scan positions (a starting point and an ending point of a scan) are acquired at each examination date, and the plural tomography images are displayed on the display unit 1. When an area by the frame K is set in at least one tomography image, an area may be set in a position on another tomography image with a different scan position to be set as the graph creation region. In this case, the area may be set in a region corresponding to the same distance with respect to a starting point and the region in which the area is set by the frame K on another tomography image with the different scan position.

Also, a similar analysis can be conducted in map data. In this case, setting of a region is not limited to an OCT image and, for example, an analytical value may be obtained by freely setting a graph creation region on a thickness map.

The embodiment described above can be represented as described below.

(1) The controller creates and displays a time-series graph using analytical values of any positions capable of being acquired from plural OCT data photographed at different dates.

(2) In the plural OCT data photographed at different dates in (1), an image is aligned with a BaseLine for each of the other data (FollowUp data) based on the first data (BaseLine). As a result of the alignment, any position set in the BaseLine is also set automatically in the FollowUp data.

(3) In (1), any two points on the OCT data are set and an analytical value obtained from the portion between the two points is used.

(4) In (1), any region on the OCT data is set and an analytical value obtained from the inside of the region is used.

(5) In any one of (1) to (4), a regression analysis of time-series data is conducted using the acquired analytical value and a slope of a straight line is displayed together with the obtained straight line.

(6) In any one of (1) to (4), a regression analysis of time-series data is conducted using the acquired analytical value and a p value is obtained from the obtained straight line and is displayed.

What is claimed is:
1. An ophthalmic analysis apparatus comprising:
a processor; and
memory storing computer readable instructions, when executed by the processor, causing the ophthalmic analysis apparatus to function as:
an obtaining unit configured to obtain analysis results of tomography images of a subject eye acquired at different dates by ophthalmic optical coherence tomography;

an instruction receiving unit configured to receive, from an examiner, selection instructions to select an analytical region on the eye; and a generating unit configured to respectively acquire analysis results in the analytical region selected by the instruction receiving unit with respect to tomography images acquired at the different dates and generate statistical information formed based on time-series data of the acquired analysis result of the tomography images acquired at the different dates;

an output unit configured to output and display the statistical information as a time-series graph, wherein an axis for abscissas defines a time axis for the time-series graph and an axis for ordinates defines the analysis results at the different dates for the time-series graph; and wherein the output unit is configured to display an analysis chart showing a fundamental statistic of the analysis results every preset section, and the instruction receiving unit is configured to receive from the selection instructions an instruction to select at least one section from the analysis chart disposed on a display and the output unit is configured to display the time-series graph corresponding to the selected section.

2. The ophthalmic analysis apparatus according to claim 1, wherein the instruction receiving unit receives, from the examiner, selection instructions for a two-dimensional image at an examination date at which an analysis result is acquired.

3. The ophthalmic analysis apparatus according to claim 2, wherein the two-dimensional image includes at least any of a tomography image, a front image, the analysis chart and an analysis map.

4. The ophthalmic analysis apparatus according to claim 1, wherein
the instruction receiving unit receives, from the examiner, selection instructions to select a one-dimensional region on the tomography image outputted to display unit, and
the generating unit acquires at least one analysis result in the selected one-dimensional region.

5. The ophthalmic analysis apparatus according to claim 1, wherein
the instruction receiving unit receives, from the examiner, selection instructions to select a two-dimensional region on the tomography image outputted to a display screen of a display unit, and
the generating unit acquires at least one analysis result in the selected two-dimensional region.

6. The ophthalmic analysis apparatus according to claim 1, wherein the instruction receiving unit receives, from the examiner, selection instructions to select at least one section divided by the analysis chart indicating a fundamental statistic of an analysis result every preset section.

7. The ophthalmic analysis apparatus according to claim 1, wherein the instruction receiving unit is configured to output to the display a section selector having a section selective region formed at a position corresponding to each section of the analysis chart, and is further configured to receive the section selection instruction from the examiner according to the section region selected on the section selector.

8. The ophthalmic analysis apparatus according to claim 1, wherein the output unit is configured to discriminatively output plural time-series graphs related to a plurality of sections in the analysis chart on the same graph, and to assign section discrimination information indicating a position on the analysis chart of the section outputted to the time-series graph.

9. An ophthalmic analysis apparatus comprising:
a processor; and
memory storing computer readable instruction, when executed by the processor, causing the ophthalmic analysis apparatus to function as:
an obtaining unit configured to obtain analysis results of tomography images of a subject eye acquired at different dates by ophthalmic optical coherence tomography;
a generating unit configured to generate statistical information based on time-series data of the acquired analysis result of the tomography images acquired at the different dates;
an output unit configured to display statistical information as a time-series graph, wherein an axis for abscissas defines a time axis for the time-series graph and an axis for ordinates defines the analysis results at the different dates for the time-series graph;
an event receiving unit configured to receive an input of occurrence time of an event related to an eye disease of a subject and a name of the event, and
a controller configured to add, to the statistical information, information indicating occurrence of the event in a position corresponding to the occurrence time received by the event receiving unit, and to output image data including the statistical information to which the information indicating occurrence of the event is added and a name of the event received by the event information receiving unit;
wherein the controller outputs another time-series graph including time-series data of an analysis result obtained by another ophthalmic apparatus different from optical coherence tomography for fundus photograph together with the time-series graph.

10. The ophthalmic analysis apparatus according to claim 9, wherein the generating unit conducts a first regression analysis for conducting a regression analysis of the time-series data before the occurrence time and conducts a second regression analysis for conducting a regression analysis of the time-series data after the event occurrence time based on the occurrence time received by the event receiving unit, and outputs a trend graph including a first trend graph by the first regression analysis and a second trend graph by the second regression analysis as the statistical information.

11. The ophthalmic analysis apparatus according to claim 9, wherein the controller assigns and outputs elapsed time from an examination date or the occurrence time to a region in which a time axis in the time-series graph is represented.

12. The ophthalmic analysis apparatus according to claim 9, wherein the generating unit conducts a first regression analysis for conducting a regression analysis of the time-series data before the occurrence time and conducts a second regression analysis for conducting a regression analysis of the time-series data after the event occurrence time based on the occurrence time received by the event receiving unit, and displays a slope by the first regression analysis and a slope by the second regression analysis so that the slope by the first regression analysis can be compared with the slope by the second regression analysis.

13. The ophthalmic analysis apparatus according to claim 9, wherein the controller displays the time-series graph of the eye and a normal eye time-series graph formed based on time-series data of a normal eye so that the time-series graph of the eye can be compared with the normal eye time-series graph.

14. The ophthalmic analysis apparatus according to claim 9, wherein the controller outputs positional information indicating a position on a fundus of an analysis result outputted to the time-series graph together with the time-series graph.

15. An ophthalmic analysis apparatus comprising:
a processor; and
memory storing computer readable instruction, when executed by the processor, causing the ophthalmic analysis apparatus to function as:
an obtaining unit configured to obtain analysis results of tomography images of a subject eye acquired at different dates by ophthalmic optical coherence tomography;
a generating unit configured to generate statistical information based on time-series data of the acquired analysis result of the tomography images acquired at the different dates;
an output unit configured to display statistical information as a time-series graph wherein an axis for abscissas defines a time axis for the time-series graph and an axis for ordinates defines the analysis results at the different dates for the time-series graph;
an instruction receiving unit configured to receive, from an examiner, selection instructions to select plural two-dimensional images outputted as plural two-dimensional images at each examination date for a specific period on the statistical information; and
a controller configured to output an image data in which the plural two-dimensional images selected by the instruction receiving unit are arranged together with the statistical information; and
wherein the output unit is configured to display an analysis chart showing a fundamental statistic of the analysis results every preset section, and the instruction receiving unit is configured to receive from the selection instructions an instruction to select at least one section from the analysis chart disposed on a display and the output unit is configured to display the time-series graph corresponding to the selected section.

16. The ophthalmic analysis apparatus according to claim 15, wherein the instruction receiving unit receives, from the examiner, change instructions to change a two-dimensional image displayed on a display unit, and the controller changes the two-dimensional image displayed on the display unit according to change instructions from the instruction receiving unit.

17. The ophthalmic analysis apparatus according to claim 16, wherein the instruction receiving unit receives, from the examiner, the selection instructions to select at least one of the two-dimensional images displayed on the display unit as a fixed display image, and the controller changes and displays another two-dimensional image different from the fixed image according to change instructions from the instruction receiving unit while fixing the display of the two-dimensional image selected as the fixed display image.

18. A non-transitory computer readable recording medium storing computer readable instructions, when executed by a processor, causing an ophthalmic analysis apparatus to function as:
an obtaining unit configured to obtain analysis results of tomography images of a subject eye acquired at different dates by ophthalmic optical coherence tomography;
an instruction receiving unit configured to receive, from an examiner, selection instructions to select an analytical region on the eye; and
a controller configured to respectively acquire analysis results in the analytical region selected by the instruction receiving unit with respect to tomography images acquired at the different dates and generate statistical information formed based on time-series data of the acquired analysis result of the tomography images acquired at the different dates; and
an output unit configured to output and display as a times-series graph the generated statistical information wherein an axis for abscissas defines a time axis for the time-series graph and an axis for ordinates defines the analysis results at the different dates for the time-series graph; and
wherein the output unit displays an analysis chart showing a fundamental statistic of the analysis results every preset section, and the instruction receiving unit receives from the selection instructions an instruction to select at least one section from the analysis chart disposed on a display and the output unit displays the time-series graph corresponding to the selected section.

* * * * *